US008921415B2

(12) United States Patent
Marom

(10) Patent No.: US 8,921,415 B2
(45) Date of Patent: Dec. 30, 2014

(54) POLYMORPHS OF DARUNAVIR

(75) Inventor: Ehud Marom, Kfar Saba (IL)

(73) Assignee: Mapi Pharma Ltd., Ness Ziona (IL)

(*) Notice: Subject to any disclaimer, the term of this patent is extended or adjusted under 35 U.S.C. 154(b) by 60 days.

(21) Appl. No.: 13/557,991

(22) Filed: Jul. 25, 2012

(65) Prior Publication Data

US 2013/0023570 A1 Jan. 24, 2013

Related U.S. Application Data

(63) Continuation-in-part of application No. 13/146,727, filed as application No. PCT/IL2009/001158 on Dec. 8, 2009.

(60) Provisional application No. 61/148,055, filed on Jan. 29, 2009, provisional application No. 61/242,818, filed on Sep. 16, 2009.

(51) Int. Cl.
*A61K 31/34* (2006.01)
*C07D 493/04* (2006.01)
*A61K 45/06* (2006.01)
*A61K 31/427* (2006.01)

(52) U.S. Cl.
CPC ............... *A61K 31/34* (2013.01); *C07D 493/04* (2013.01); *A61K 45/06* (2013.01); *A61K 31/427* (2013.01)
USPC .......................................... 514/465; 549/464

(58) Field of Classification Search
CPC .............................. A61K 31/34; C07D 493/04
USPC ................................ 514/470, 465; 549/464
See application file for complete search history.

(56) References Cited

U.S. PATENT DOCUMENTS

| | | | |
|---|---|---|---|
| 4,415,747 A | 11/1983 | Kaplan |
| 5,744,481 A | 4/1998 | Vazquez et al. |
| 5,786,483 A | 7/1998 | Vazquez et al. |
| 5,830,897 A | 11/1998 | Vazquez et al. |
| 5,843,946 A | 12/1998 | Vazquez et al. |
| 5,968,942 A | 10/1999 | Vazquez et al. |
| 6,037,157 A | 3/2000 | Norbeck et al. |
| 6,046,190 A | 4/2000 | Vazquez et al. |
| 6,060,476 A | 5/2000 | Vazquez et al. |
| 6,172,082 B1 | 1/2001 | Vazquez et al. |
| 6,248,775 B1 | 6/2001 | Vazquez et al. |
| 6,335,460 B1 | 1/2002 | Vazquez et al. |
| 6,417,387 B1 | 7/2002 | Vazquez et al. |
| 6,455,581 B1 | 9/2002 | Vazquez et al. |
| 6,472,407 B1 | 10/2002 | Vazquez et al. |
| 6,500,832 B1 | 12/2002 | Vazquez et al. |
| 6,534,493 B1 | 3/2003 | Vazquez et al. |
| 6,613,743 B2 | 9/2003 | Hale et al. |
| 6,646,010 B2 | 11/2003 | Vazquez et al. |
| 6,703,403 B2 | 3/2004 | Norbeck et al. |
| 6,846,954 B2 | 1/2005 | Vazquez et al. |
| 6,852,887 B2 | 2/2005 | Malik et al. |
| 6,919,465 B2 | 7/2005 | Ghosh et al. |
| 6,924,286 B1 | 8/2005 | Vazquez et al. |
| 7,115,618 B2 | 10/2006 | Vazquez et al. |
| 7,141,609 B2 | 11/2006 | Vazquez et al. |
| 7,320,983 B2 | 1/2008 | Vazquez et al. |
| 7,470,506 B1 | 12/2008 | Erickson et al. |
| 7,531,538 B2 | 5/2009 | Vazquez et al. |
| 7,700,645 B2 | 4/2010 | Vermeersch et al. |
| 2002/0026079 A1 | 2/2002 | Kronenthal et al. |
| 2004/0127727 A1 | 7/2004 | Ghosh et al. |
| 2004/0162340 A1 | 8/2004 | Ikemoto et al. |
| 2005/0089164 A1 | 4/2005 | Lang et al. |
| 2005/0250845 A1 | 11/2005 | Vermeersch et al. |
| 2005/0256322 A1 | 11/2005 | Ikemoto et al. |
| 2006/0135562 A1 | 6/2006 | Kraft |
| 2006/0135563 A1 | 6/2006 | Kraft et al. |
| 2006/0148865 A1 | 7/2006 | Martin et al. |
| 2007/0060642 A1 | 3/2007 | Goyvaerts et al. |
| 2009/0131363 A1 | 5/2009 | Harbeson |
| 2010/0168422 A1 | 7/2010 | Chen |
| 2012/0035142 A1 | 2/2012 | Marom |

FOREIGN PATENT DOCUMENTS

| | | |
|---|---|---|
| CA | 2485834 A1 | 12/2003 |
| CN | 1668623 | 9/2005 |
| DE | 69332002 T2 | 12/2002 |
| EP | 0715618 | 3/1995 |
| EP | 0754669 A1 | 1/1997 |
| EP | 0810209 A2 | 12/1997 |
| EP | 1029856 A1 | 8/2000 |
| EP | 1067125 A1 | 1/2001 |
| EP | 1081133 A1 | 3/2001 |
| EP | 1215209 A1 | 6/2002 |
| EP | 1661893 A2 | 5/2006 |
| EP | 1889826 A1 | 2/2008 |
| ES | 2123065 T3 | 1/1999 |
| ES | 2127938 T3 | 5/1999 |
| ES | 2177868 T3 | 12/2002 |

(Continued)

OTHER PUBLICATIONS

Brittain, H. G., 1999, Polymorphism in Pharmaceutical Solids, CRC Press, New York City, p. 184-226.
Supplementary European Search Report dated May 21, 2012 of European Patent Application No. 09839083.4.
European Office Action dated Jan. 24, 2013 of European Patent Application No. 09839083.4.
English translation of Chinese Office Action dated Jan. 24, 2013 of Chinese Patent Application No. 200980155801.2.
Beaulieu, Pierre L. et al., (1995) "Large scale preparation of (2S,3S)-N-Boc-3-amino-1,2-epoxy-4-phenylbutane: A key building block for HIV-protease inhibitors," Tetrahedron Letters, 1995, 36(19):3317-3320.
Bull, Steven D. et al.,(1998) "Chiral relay auxiliaries," Pure & App. Chem. 70(8):1501-1506.

(Continued)

*Primary Examiner* — Taofiq A Solola
(74) *Attorney, Agent, or Firm* — Rothwell, Figg, Ernst & Manbeck, P.C.

(57) ABSTRACT

The present invention provides new pseudopolymorphic forms of darunavir as well as a novel amorphous form of darunavir, pharmaceutical compositions comprising these compounds, methods for their preparation and use thereof in treating retroviral infections, in particular, HIV infection.

9 Claims, 20 Drawing Sheets

(56) References Cited

FOREIGN PATENT DOCUMENTS

| | | | |
|---|---|---|---|
| FI | 119427 | B | 11/2008 |
| JP | 09124629 | A | 5/1997 |
| WO | 94/04492 | A1 | 3/1994 |
| WO | 9404492 | A1 | 3/1994 |
| WO | 9506030 | A1 | 3/1995 |
| WO | 99/67254 | A2 | 12/1999 |
| WO | 99/67417 | A2 | 12/1999 |
| WO | 03/022853 | A1 | 3/2003 |
| WO | 03/024974 | A2 | 3/2003 |
| WO | 03/060905 | A1 | 7/2003 |
| WO | 03/106461 | A2 | 12/2003 |
| WO | 2004/016619 | A1 | 2/2004 |
| WO | 2004/033462 | A2 | 4/2004 |
| WO | 2004/094465 | A2 | 11/2004 |
| WO | 2005/000249 | A2 | 1/2005 |
| WO | 2005/063770 | A1 | 7/2005 |
| WO | 2005/087728 | A1 | 9/2005 |
| WO | 2005/095410 | A1 | 10/2005 |
| WO | 2005/110428 | A2 | 11/2005 |
| WO | 2006/108879 | A2 | 10/2006 |
| WO | 2006/132390 | A1 | 12/2006 |
| WO | 2007/060253 | A1 | 5/2007 |
| WO | 2007/126812 | A2 | 11/2007 |
| WO | 2008/016522 | A2 | 2/2008 |
| WO | 2008/034598 | A1 | 3/2008 |
| WO | 2008/055970 | A2 | 5/2008 |
| WO | 2008/132154 | A1 | 11/2008 |
| WO | 2009/000853 | A2 | 12/2008 |
| WO | 2009/005674 | A2 | 1/2009 |
| WO | 2009/030733 | A1 | 3/2009 |
| WO | 2009/081174 | A2 | 7/2009 |
| WO | 2010/002998 | A1 | 1/2010 |
| WO | 2010/023322 | A1 | 3/2010 |
| WO | 2010/086844 | A1 | 8/2010 |
| WO | 2011/048604 | A2 | 4/2011 |
| WO | 2011/051978 | A2 | 5/2011 |
| WO | 2011/073993 | A1 | 6/2011 |
| WO | 2011/083287 | A2 | 7/2011 |
| WO | 2011/092687 | A1 | 8/2011 |
| WO | 2011/141921 | A1 | 11/2011 |

OTHER PUBLICATIONS

Cohen, Noal et al., (1983) "Enantiospecific syntheses of leukotrienes C4, D4, and E4, and [14,15-3H2]leukotriene E4 dimethyl ester," J. Am. Chem. Soc. 105(11):3661-3672.
Contreras, Jordi et al., (1980) "Synthesis of Poly(p-Benzenesulphonamide) Part I. Preparation of Sulphanilic Acid Derivatives for Use as Intermediates," British Polymer Journal, pp. 192-198.
Ghosh, Arun K. et al., (1998) "Potent HIV protease inhibitors incorporating high-affinity P2-ligands and (R)-(hydroxyethylamino)sulfonamide isostere," Bioorg Med Chem Lett 8, pp. 687-690.
Ghosh, Arun K. et al., (2004) "Stereoselective Photochemical 1,3-Dioxolane Addition to 5-Alkoxymethyl-2(5H)-furanone: Synthesis of Bis-tetrahydrofuranyl Ligand for HIV Protease Inhibitor UIC-94017 (TMC-114)," J. Org Chem. 69(23):7822-7829.
Gioeli, Carlo et al., (1982) "The flouren-9-ylmethoxycarbonyl group for the protection of hydroxy-groups; its application in the synthesis of an octathymidylic acid fragment," J Chem Soc, Chem commun, pp. 672-674.
Griffith, William P. et al., (1987) "Preparation and use of tetra-n-butylammonium per-ruthenate (TBAP reagent) and tetra-n-propylammonium per-ruthenate (TPAP reagent) as new catalytic oxidants for alcohols," J. Chem. Soc. Chem Commun., pp. 1625-1627.
Guanti, Giuseppe et al., (2002) "O-Protecting groups as long-range stereocontrolling elements in the addition of acetylides to 4-substituted quinolines," Tetrahedron: Asymmetry 13:2703-2726.
Honda, Yutaka et al., (2004) "New approaches to the industrial synthesis of HIV protease inhibitors," Org. Biomol. Chem. 2:2061-2070.
Li, Hui-Zhang et al., (2003) "A study on the sulfonation of aromatic amines with sulfuric acid under microwave irradiation," Journal of Chemical Research, Synopses, pp. 493-494.
Miller, John F. et al., (2004) "Novel arylsulfonamides possessing sub-picomolar HIV protease activities and potent anti-HIV activity against wild-type and drug-resistant viral strains," Bioorg Med Chem Lett 14:959-963.
Steffan, Robert J. et al., (2002) "Novel substituted 4-aminomethylpiperidines as potent and selective human beta3-agonists. Part 2: arylethanolaminomethylpiperidines," Bioorg Med Chem Lett 12:2963-2967.
Surleraux, Dominic L. N. G. et al., (2005) "Discovery and selection of TMC114, a next generation HIV-1 protease inhibitor," J Med Chem 48(6):1813-1822.
Wenger, Ronald Maurice (1985) "Synthesis of Cyclosporine and Analogues: Structural Requirements for Immunosuppressive Activity," Angew. Chem. Int. Ed. Eng. 24(2):77-85.
International Search Report issued in International Application No. PCT/IL09/01158 mailed Apr. 23, 2010, 1 page.
S. Byrn et al., (1995) "Pharmaceutical solids: a strategic approach to regulatory considerations," Pharm Res 12(7): 945-954.
D.J.W. Grant (1999) "Theory and Origin of Polymorphism". In: Polymorphism in Pharmaceutical Solids, edited by Brittain HG, CRC Press, New York City, pp. 1-10.
N.K. Jain et al. (1986) Polymorphism in pharmacy. Indian Drugs 23(6): 315-329.
A.W. Newman et al., (2003) Solid-state analysis of the active pharmaceutical ingredient in drug product. Drug Discov Today 8(19): 898-905.

POLYMORPHS OF DARUNAVIR

CROSS REFERENCE TO RELATED APPLICATIONS

This application is a continuation-in-part of U.S. patent application Ser. No. 13/146,727, filed on Oct. 7, 2011, which is a 35 U.S.C. §371 National Phase Entry Application from PCT/IL2009/001158, filed on Dec. 8, 2009, and designating the United States, which claims the benefit of U.S. Provisional Application No. 61/148,055, filed on Jan. 29, 2009 and the benefit of U.S. Provisional Application No. 61/242,818, filed on Sep. 16, 2009, which are incorporated herein in their entireties.

FIELD OF THE INVENTION

The present invention relates to new forms of darunavir, pharmaceutical compositions comprising same, and use thereof in treating retroviral infections.

BACKGROUND OF THE INVENTION

Darunavir is a second-generation protease inhibitor used for treating human immunodeficiency virus (HIV) infection. Co-administration of darunavir with the antiretroviral drug ritonavir was approved by the FDA in 2006 for the treatment of HIV patients who have already been administered with other antiretroviral drugs.

Darunavir is chemically named [(1S,2R)-3-[[(4-aminophenyl)sulfonyl](2-methylpropyl)amino]-2-hydroxy-1-(phenylmethyl)propyl]-carbamic acid (3R,3aS,6aR)-hexahydrofuro[2,3-b]furan-3-yl ester, and is represented by the following chemical structure:

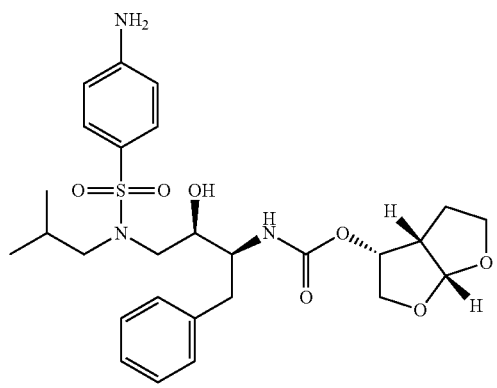 [SMILES: CC(C)CN(C[C@@H](O)[C@H](Cc1ccccc1)NC(=O)O[C@H]1CO[C@H]2OCC[C@H]21)S(=O)(=O)c1ccc(N)cc1]

Darunavir and processes for its preparation are disclosed in EP 715618, WO 99/67417, U.S. Pat. No. 5,968,942, U.S. Pat. No. 6,248,775 and in Bioorganic and Chemistry Letters, 8, 687-690, 1998.

Several pseudopolymorphic forms of darunavir are described in US 2005/0250845 including the ethanolate, hydrate, methanolate, acetonate, dichloromethanate, ethylacetate solvate, 1-methoxy-2-propanolate, anisolate, tetrahydrofuranate, isopropanolate and mesylate solvates of darunavir.

Darunavir ethanolate is marketed in the United States under the trade name PREZISTA® by Tibotec. PREZISTA® is available as an orange, oval-shaped, film coated tablet for oral administration. Darunavir monoethanolate solvate is a white to off-white powder with solubility of approximately 0.15 mg/mL in water at 20° C.

A new form of a compound may possess physical properties that differ from, and are advantageous over, those of other crystalline or amorphous forms. These include, packing properties such as molar volume, density and hygroscopicity; thermodynamic properties such as melting temperature, vapor pressure and solubility; kinetic properties such as dissolution rate and stability under various storage conditions; surface properties such as surface area, wettability, interfacial tension and shape; mechanical properties such as hardness, tensile strength, compactability, handling, flow and blend; and filtration properties. Variations in any one of these properties affect the chemical and pharmaceutical processing of a compound as well as its bioavailability and may often render the new form advantageous for medical use.

There still remains an unmet need for additional solid state forms of darunavir having good physiochemical properties, desirable bioavailability, and advantageous pharmaceutical parameters.

SUMMARY OF THE INVENTION

The present invention provides new polymorphic forms of darunavir, as well as a novel amorphous form of darunavir, pharmaceutical compositions comprising said compounds, methods for their preparation and use thereof in treating retroviral infections and, in particular, HIV infection.

The present invention is based in part on the unexpected finding that the new forms disclosed herein possess advantageous physicochemical properties which render their processing as medicaments beneficial. The forms of the present invention have good bioavailability as well as desirable stability characteristics enabling their incorporation into a variety of different formulations particularly suitable for pharmaceutical utility.

According to one aspect, the present invention provides a crystalline tetrahydrofuran solvate of darunavir having an X-ray powder diffraction pattern with diffraction peaks at 2-theta values of about 22.8±0.1 and 16.4±0.1.

In one embodiment, the present invention provides a crystalline tetrahydrofuran solvate of darunavir having an X-ray powder diffraction pattern with diffraction peaks at 2-theta values of about 22.8±0.1, 16.4±0.1, 22.4±0.1 and 20.9±0.1.

In another embodiment, the present invention provides a crystalline tetrahydrofuran solvate of darunavir having at least 3 X-ray diffraction peaks selected from about 6.9±0.1, 11.0±0.1, 13.6±0.1, 16.1±0.1, 16.4±0.1, 17.1±0.1, 18.4±0.1, 20.2±0.1, 20.9±0.1, 22.4±0.1, 22.8±0.1 and 23.2±0.1 degrees 2-theta.

In particular embodiments, the present invention provides a crystalline tetrahydrofuran solvate of darunavir having an X-ray powder diffraction pattern with diffraction peaks at 2-theta values of about 6.9±0.1, 11.0±0.1, 13.6±0.1, 16.1±0.1, 16.4±0.1, 17.1±0.1, 18.4±0.1, 20.2±0.1, 20.9±0.1, 22.4±0.1, 22.8±0.1 and 23.2±0.1.

According to another aspect, the present invention provides a crystalline dimethylsulfoxide solvate of darunavir having an X-ray powder diffraction pattern with diffraction peaks at 2-theta values of about 20.6±0.1 and 21.2±0.1.

In some embodiments, the present invention provides a crystalline dimethylsulfoxide solvate of darunavir having an X-ray powder diffraction pattern with diffraction peaks at 2-theta values of about 20.6±0.1, 21.2±0.1, 16.6±0.1 and 23.0±0.1.

In other embodiments, the present invention provides a crystalline dimethylsulfoxide solvate of darunavir having at least 3 X-ray diffraction peaks selected from about 7.1±0.1, 9.3±0.1, 10.6±0.1, 11.4±0.1, 13.9±0.1, 16.6±0.1, 17.3±0.1, 18.5±0.1, 20.1±0.1, 20.6±0.1, 21.2±0.1, 23.0±0.1, 27.1±0.1 and 28.1±0.1 degrees 2-theta.

In particular embodiments, the present invention provides a crystalline dimethylsulfoxide solvate of darunavir having an X-ray powder diffraction pattern with diffraction peaks at 2-theta values of about 7.1±0.1, 9.3±0.1, 10.6±0.1, 11.4±0.1, 13.9±0.1, 16.6±0.1, 17.3±0.1, 18.5±0.1, 20.1±0.1, 20.6±0.1, 21.2±0.1, 23.0±0.1, 27.1±0.1 and 28.1±0.1.

In some embodiments, the crystalline dimethylsulfoxide solvate of darunavir is in a micronized form. In some embodiments, the particle size distribution of the micronized form is such that its $D_{90}$ is less than about 9 µm. In other embodiments, the particle size distribution of the micronized form is such that its $D_{50}$ is less than about 4 µm. In other embodiments, the particle size distribution of the micronized form is such that its $D_{10}$ less than about 2 µm. In some embodiments, the $D_{10}$ of the micronized form is about 1.5 µm, its $D_{50}$ is about 3.7 µm and its $D_{90}$ is about 7.2 µm. This is in contrast to the non-micronized form of the dimethylsulfoxide solvate, which has a $D_{90}$ of less than about 100 µm, a $D_{50}$ of about 29 µm and a $D_{10}$ of about 4 µm. As demonstrated herein, the micronized form of darunavir dimethylsulfoxide solvate has an improved intrinsic dissolution profile as compared with the non-micronized form.

In yet another aspect, the present invention provides an amorphous form of darunavir having an IR spectrum with characteristic peaks at about 1454 and 1369 cm$^{-1}$. In certain embodiments, the amorphous form of darunavir has an IR spectrum with characteristic peaks at about 1454, 1369, 771 and 553 cm$^{-1}$.

In specific embodiments, the present invention provides a pharmaceutical composition comprising as an active ingredient any one of the darunavir forms of the present invention, and a pharmaceutically acceptable carrier.

In a particular embodiment, the pharmaceutical composition is in the form of a tablet.

In various embodiments, the present invention provides a pharmaceutical composition comprising as an active ingredient any one of the darunavir forms of the present invention, and a pharmaceutically acceptable carrier for use in treating retroviral infections.

In particular embodiments, the retroviral infection is a human immunodeficiency virus (HIV) infection.

In other embodiments, the pharmaceutical composition of the present invention is co-administered in combination with another antiretroviral drug. An exemplary and non-limiting embodiment is the co-administration with ritonavir.

In some embodiments, the present invention provides a method of inhibiting retrovirus protease activity comprising administering to a subject in need thereof an effective amount of a composition comprising any one of the darunavir forms of the present invention.

In additional embodiments, the present invention provides use of any one of the darunavir forms of the present invention for the preparation of a medicament for inhibiting retrovirus protease activity.

In particular embodiments, the method and use disclosed herein are designated for inhibiting HIV protease activity.

In specific embodiments, the subject is a mammal, preferably a human.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
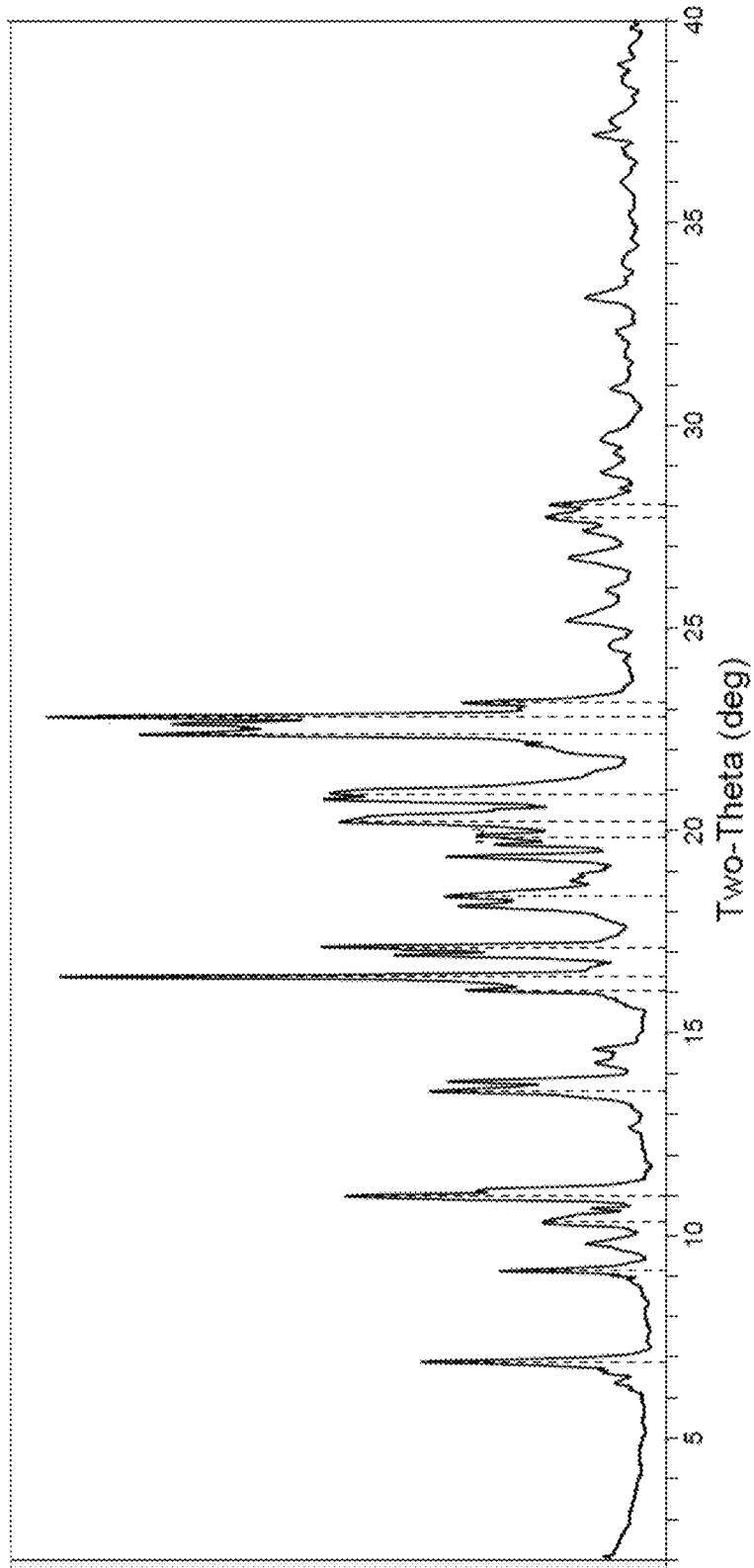
FIG. 1 is a characteristic X-ray diffraction pattern of the crystalline tetrahydrofuran solvate of darunavir.

The present invention is directed to novel pseudopolymorphic and amorphous forms of [(1S,2R)-3-[[(4-aminophenyl)

sulfonyl](2-methylpropyl)amino]-2-hydroxy-1-(phenylmethyl)propyl]-carbamic acid (3R,3aS,6aR)-hexahydrofuro[2,3-b]furan-3-yl ester having structural formula:

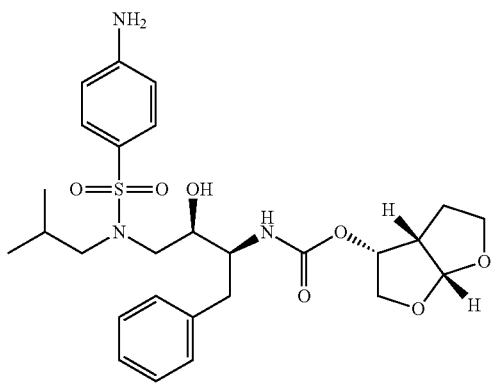 [SMILES: CC(C)CN(C[C@@H](O)[C@H](Cc1ccccc1)NC(=O)O[C@H]1CO[C@H]2OCC[C@H]21)S(=O)(=O)c1ccc(N)cc1]

The present invention is further directed to pharmaceutical compositions comprising the pseudopolymorphic forms, as well as the novel amorphous form of the compound of the present invention and a pharmaceutically acceptable carrier and their use in treating retroviral infections.

Polymorphs are two or more solid state phases of the same chemical compound that possess different arrangement and/or conformation of the molecules. Pseudopolymorphs are polymorphs which incorporate one or more solvents into the structure. Different polymorphs and pseudopolymorphs of an active pharmaceutical compound can exhibit different physical and chemical properties such as color, stability, processability, dissolution and even bioavailability.

An important physical property of a compound used as an active ingredient of a medicament is the stability at ambient conditions, especially to moisture, and under storage conditions. The identification and characterization of various polymorphs and pseudopolymorphs of a pharmaceutically active compound is therefore of great significance in obtaining medicaments with desired properties including a specific dissolution rate, milling property, bulk density, thermal stability or shelf-life. The darunavir forms of the present invention possess improved characteristics of hygroscopicity, bulk density and solubility in aqueous media. Furthermore, the darunavir forms of the present invention have improved chemical and solid state stability. Hence, these forms may be more stable when stored over prolonged periods of time.

In one embodiment, the present invention relates to crystalline tetrahydrofuran solvates of darunavir having any stoichiometry from 0.5 tetrahydrofuran to 5.0 molecules of tetrahydrofuran per molecule of darunavir. Exemplary stoichiometries are hemisolvates, monosolvates, disolvates or trisolvates.

Provided herein is a crystalline tetrahydrofuran solvate of darunavir which is characterized by a unique X-ray diffraction pattern having characteristic peaks expressed in degrees 2-theta at about 22.8±0.1 and 16.4±0.1. Preferably, the X-ray diffraction pattern has additional characteristic peaks expressed in degrees 2-theta at about 22.4±0.1 and 20.9±0.1. More preferably, the X-ray diffraction pattern has additional characteristic peaks expressed in degrees 2-theta at about 11.0±0.1, 17.1±0.1 and 20.2±0.1. Most preferably, the X-ray diffraction pattern has characteristic peaks expressed in degrees 2-theta at about 6.9±0.1, 11.0±0.1, 13.6±0.1, 16.1±0.1, 16.4±0.1, 17.1±0.1, 18.4±0.1, 20.2±0.1, 20.9±0.1, 22.4±0.1, 22.8±0.1 and 23.2±0.1.

The crystalline form of darunavir tetrahydrofuran solvate of the present invention can be further characterized by its melting point and by using various techniques including infrared absorption, Raman spectrometry, solid state NMR, and thermal analysis (e.g. thermogravimetric analysis (TGA) and differential scanning calorimetry (DSC)).

Specifically, the crystalline tetrahydrofuran solvate of darunavir of the present invention is characterized by TGA as having an approximately 9-11% weight loss at a temperature range of room temperature (RT) to 200° C. substantially attributed to solvate release. The form is further characterized by Infrared spectroscopy to have characteristic peaks and their relative intensities[1] at the following wavenumbers: 3437m, 3348s, 3253m, 3062vw, 3030vw, 2961m, 2901w, 2872w, 1704vs, 1646w, 1596vs, 1548m, 1503m, 1455w, 1368w, 1342m, 1317s, 1263s, 1244m, 1227w, 1185w, 1153vs, 1090m, 1044m, 1021m, 988m, 944m, 910w, 885vw, 862vw, 839w, 767m, 741m, 698w, 673m, 632w, 581m, 554s, and 502vw cm$^{-1}$.

[1] vs=very strong, s=strong, m=medium, w=weak, vw=very weak, br=broad.

The present invention further relates to crystalline dimethylsulfoxide solvates of darunavir having any stoichiometry from 0.5 dimethylsulfoxide to 5.0 molecules of dimethylsulfoxide per molecule of darunavir. Particular stoichiometries are hemisolvates, monosolvates, disolvates or trisolvates.

Provided herein is a crystalline dimethylsulfoxide solvate of darunavir which is characterized by a unique X-ray diffraction pattern having characteristic peaks expressed in degrees 2-theta at about 20.6±0.1 and 21.2±0.1. Preferably, the X-ray diffraction pattern has additional characteristic peaks expressed in degrees 2-theta at about 16.6±0.1 and 23.0±0.1. More preferably, the X-ray diffraction pattern has additional characteristic peaks expressed in degrees 2-theta at about 18.5±0.1 and 17.3±0.1. Most preferably, the X-ray diffraction pattern has characteristic peaks expressed in degrees 2-theta at about 7.1±0.1, 9.3±0.1, 10.6±0.1, 11.4±0.1, 13.9±0.1, 16.6±0.1, 17.3±0.1, 18.5±0.1, 20.1±0.1, 20.6±0.1, 21.2±0.1, 23.0±0.1, 27.1±0.1 and 28.1±0.1.

Additionally, the crystalline form of darunavir dimethylsulfoxide solvate is characterized by an about 10-12% weight loss at a temperature range of RT to 230° C. substantially attributed to solvate release. The form is further characterized by Infrared spectroscopy with characteristic peaks and their relative intensities[2] at 3407br, 3342s, 3250m, 3062vw, 3026vw, 2962m, 2901w, 2872w, 1704vs, 1646w, 1596vs, 1546m, 1500m, 1467w, 1454w, 1372m, 1340m, 1311s, 1263s, 1244m, 1227w, 1183w, 1155vs, 1091m, 1043m, 1023m, 988m, 947m, 891w, 862vw, 842w, 769m, 744m, 700w, 671m, 554s, and 502vw cm$^{-1}$.

The present invention further relates to amorphous darunavir characterized by an X-ray diffraction pattern having a single broad peak expressed between 10 and 25 [2θ°]. The amorphous darunavir of the present invention is further characterized by IR peaks and their relative intensities[2] at the following wavenumbers: 3466br, 3386s, 3250m, 3066vw, 3026vw, 2960m, 2901w, 2872w, 1706vs, 1633m, 1597vs, 1537m, 1503m, 1454w, 1369w, 1315s, 1260m, 1149vs, 1091s, 1041m, 1017m, 937w, 885vw, 833w, 771m, 702m, 673m, 632w, and 553s cm$^{-1}$.

[2] vs=very strong, s=strong, m=medium, w=weak, vw=very weak, br=broad.

The crystalline pseudopolymorphic forms of the present invention as well as the novel amorphous form can be prepared by a variety of methods, including for example, crystallization/precipitation or recrystallization from a suitable solvent, sublimation, growth from a melt, solid state transformation from another phase, crystallization/precipitation from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. The term "antisolvent" as used herein refers to a solvent in which the compound has low solubility.

Suitable solvents and anti-solvents for preparing crystals include polar and nonpolar solvents. The choice of solvent or solvents is typically dependent upon one or more factors, including solubility of the compound in such solvent, crystallization technique, and vapor pressure of the solvent. Combinations of solvents may be employed; for example, the compound may be solubilized into a first solvent followed by the addition of an antisolvent to decrease the solubility of the compound in the solution and to induce crystallization. Suitable solvents include, but are not limited to, polar aprotic solvents and polar protic solvents, and mixtures thereof. Particular examples of suitable polar aprotic solvents include, but are not limited to, acetonitrile, tetrahydrofuran (THF), dichloromethane, acetone, dimethylformamide, and dimethylsulfoxide.

Seed crystals may be added to any crystallization mixture to promote crystallization as is known in the art. Alternatively, crystalline forms may be obtained by distillation or solvent addition techniques such as those known to those skilled in the art. Suitable solvents for this purpose include any of those solvents described herein, including protic polar solvents, such as alcohols (for example, methanol, ethanol, and isopropanol), aprotic polar solvents (including those listed above), and also ketones (for example, acetone, methyl ethyl ketone, and methyl isobutyl ketone).

Exemplary processes used to prepare each of the pseudopolymorphic darunavir forms of the present invention are provided herein.

Methods for "crystallization from solution" include, but are not limited to, a concentration method, a slow cooling method, a reaction method (diffusion method, electrolysis method), a hydrothermal growth method, a fusing agent method, and so forth. The solution can be a supersaturated solution, optionally heated to temperatures bellow the solvent boiling point. The recovery of the solid state forms can be done for example, by filtering the suspension and drying.

In particular, the darunavir forms of the present invention can be prepared by the slurry method as is well known in the art. Suspensions of the active ingredient in different solvents or mixture of solvents are prepared and shaken for long intervals (typically 24 hours).

The darunavir forms of the present invention can be prepared using slow precipitation from saturated solutions in different solvents or mixture of solvents which are allowed to evaporate at room temperatures. Alternatively the saturated solutions can be heated followed by their cooling to induce precipitation as is known in the art.

Encompassed by the present invention are methods of antisolvent precipitation where an antisolvent is added to the saturated solution of the active ingredient in different solvents or mixture of solvents to induce precipitation.

Within the scope of the present invention are high pressure techniques where the active ingredient is compressed using various forces as is known in the art.

The novel crystalline and amorphous forms of darunavir may be in a micronized or non-micronized form, wherein micronized forms are generally characterized by an improved intrinsic dissolution rate as compared with the non-micronized form.

Numerous processes are known in the art for preparing drug formulations having particle sizes in a desired range, or having a desired mean particle size, or having a particle size distribution characterized by a parameter such as $D_{90}$, which is defined herein as a linear measure of diameter having a value such that 90% by weight of particles in the formulation, in the longest dimension of the particles, are smaller than that diameter. Other particle size parameters used herein are defined in similar fashion; for example $D_{10}$ and $D_{50}$ parameters relate to linear measures of diameter having values such that 10% and 50% respectively by weight are smaller than that diameter.

For example, the micronized forms can be prepared by milling or grinding, or any other process known to reduce particle size. Various conventional mills or grinders can be used, for example impact milling such as pin milling provides improved blend uniformity to the final composition relative to other types of milling Cooling of the material being milled, for example, using liquid nitrogen, may be advantageous during milling to avoid heating the compound to undesirable temperatures. The D particle size during this milling step is preferably reduced to less than about 25 µm, more preferably less than about 10 µm.

For example, in some embodiments, the present invention provides a crystalline dimethylsulfoxide solvate of darunavir which is in a micronized form. In some embodiments, the particle size distribution of the micronized form is such that its $D_{90}$ is less than about 9 µm. In other embodiments, the particle size distribution of the micronized form is such that its $D_{50}$ is less than about 4 µm. In other embodiments, the particle size distribution of the micronized form is such that its $D_{10}$ is less than about 2 µm. In some embodiments, the $D_{10}$ of the micronized form is about 1.5 µm, its $D_{50}$ is about 3.7 µm and its $D_{90}$ is about 7.2 µm. This is in contrast to the non-micronized form of the dimethylsulfoxide solvate, which has a $D_{90}$ of less than about 100 µm, $D_{50}$ of about 29 µm and $D_{10}$ of about 4 µm.

In other embodiments, the present invention provides a crystalline tetrahydrofuran solvate of darunavir which is in a micronized form. In other embodiments, the present invention provides an amorphous form of darunavir which is in a micronized form. Each possibility represents a separate embodiment of the present invention.

The novel forms of darunavir are useful as pharmaceuticals for inhibiting retroviral infections. The present invention thus provides pharmaceutical compositions comprising the pseudopolymorphs and amorphous form disclosed herein and a pharmaceutically acceptable carrier. The solid state polymorphs of the present invention can be safely administered orally or non-orally (e.g., topical, rectal). The pharmaceutical compositions can be formulated as tablets (including sugar-coated tablets and film-coated tablets), powders, granules, capsules (including soft capsules), orally disintegrating tablets, and sustained-release preparations as is well known in the art.

Pharmacologically acceptable carriers that may be used in the context of the present invention include various organic or inorganic carriers including, but not limited to, excipients, lubricants, binders, disintegrants, water-soluble polymers and basic inorganic salts. The pharmaceutical compositions of the present invention may further include additives such as, but not limited to, preservatives, antioxidants, coloring agents, sweetening agents, souring agents, bubbling agents and flavorings.

Suitable excipients include e.g. lactose, sucrose, D-mannitol, starch, cornstarch, crystalline cellulose, light silicic anhydride and titanium oxide. Suitable lubricants include e.g.

magnesium stearate, sucrose fatty acid esters, polyethylene glycol, talc and stearic acid. Suitable binders include e.g. hydroxypropyl cellulose, hydroxypropylmethyl cellulose, crystalline cellulose, a-starch, polyvinylpyrrolidone, gum arabic powder, gelatin, pullulan and low-substitutional hydroxypropyl cellulose. Suitable disintegrants include e.g. crosslinked povidone (any crosslinked 1-ethenyl-2-pyrrolidinone homopolymer including polyvinylpyrrolidone (PVPP) and 1-vinyl-2-pyrrolidinone homopolymer), crosslinked carmellose sodium, carmellose calcium, carboxymethyl starch sodium, low-substituted hydroxypropyl cellulose, cornstarch and the like. Suitable water-soluble polymers include e.g. cellulose derivatives such as hydroxypropyl cellulose, polyvinylpyrrolidone, hydroxypropylmethyl cellulose, methyl cellulose and carboxymethyl cellulose sodium, sodium polyacrylate, polyvinyl alcohol, sodium alginate, guar gum and the like. Suitable basic inorganic salts include e.g. basic inorganic salts of sodium, potassium, magnesium and/or calcium. Particular embodiments include the basic inorganic salts of magnesium and/or calcium. Basic inorganic salts of sodium include, for example, sodium carbonate, sodium hydrogen carbonate, disodiumhydrogenphosphate, etc. Basic inorganic salts of potassium include, for example, potassium carbonate, potassium hydrogen carbonate, etc. Basic inorganic salts of magnesium include, for example, heavy magnesium carbonate, magnesium carbonate, magnesium oxide, magnesium hydroxide, magnesium metasilicate aluminate, magnesium silicate, magnesium aluminate, synthetic hydrotalcite, aluminahydroxidemagnesium and the like. Basic inorganic salts of calcium include, for example, precipitated calcium carbonate, calcium hydroxide, etc.

Suitable preservatives include e.g. sodium benzoate, benzoic acid, and sorbic acid. Suitable antioxidants include e.g. sulfites, ascorbic acid and a-tocopherol. Suitable coloring agents include e.g. food colors such as Food Color Yellow No. 5, Food Color Red No. 2 and Food Color Blue No. 2 and the like. Suitable sweetening agents include e.g. saccharin sodium, dipotassium glycyrrhetinate, aspartame, stevia and thaumatin. Suitable souring agents include e.g. citric acid (citric anhydride), tartaric acid and malic acid. Suitable bubbling agents include e.g. sodium bicarbonate. Suitable flavorings include synthetic substances or naturally occurring substances, including e.g. lemon, lime, orange, menthol and strawberry.

The solid forms of the present invention are particularly suitable for oral administration in the form of tablets, capsules, pills, dragées, powders, granules and the like. A tablet may be made by compression or molding, optionally with one or more excipients as is known in the art. Specifically, molded tablets may be made by molding in a suitable machine a mixture of the powdered active ingredient moistened with an inert liquid diluent.

The tablets and other solid dosage forms of the pharmaceutical compositions described herein may optionally be scored or prepared with coatings and shells, such as enteric coatings and other coatings well known in the art. They may also be formulated so as to provide slow or controlled release of the active ingredient therein using, for example, hydroxypropylmethyl cellulose in varying proportions to provide the desired release profile, other polymer matrices and the like. The active ingredient can also be in micro-encapsulated form, if appropriate, with one or more of the above-described excipients.

The present invention provides a method of inhibiting retrovirus protease activity comprising administering to a subject in need thereof an effective amount of a composition comprising any one of the darunavir forms of the present invention.

"A therapeutically effective amount" as used herein refers to an amount of an agent which is effective, upon single or multiple dose administration to the subject in providing a therapeutic benefit to the subject. In one embodiment, the therapeutic benefit is inhibiting retrovirus protease activity, or in prolonging the survivability of a subject with such a viral infection beyond that expected in the absence of such treatment. In additional embodiments, the darunavir forms of the present invention are used for the preparation of a medicament for treating diseases caused by retroviruses such as HIV infections, e.g. Acquired Immune Deficiency Syndrome (AIDS) and AIDS-Related Complex (ARC).

The present invention further provides the administration of the darunavir forms in combination therapy with 1 to 3 other active ingredients. Such "other active ingredients", according to the principles of the present invention include, but are not limited to, other antiretroviral drugs (e.g. Etravirine, Raltegravir, Rifabutin). In specific embodiments, the present invention provides the co-administration of darunavir with ritonavir.

It is further contemplated that the combination therapy will include the two or more active ingredients within a single pharmaceutical composition as well as the two or more active ingredients in two separate pharmaceutical compositions administered to the same subject simultaneously or at a time interval determined by a skilled artisan.

The principles of the present invention are demonstrated by means of the following non-limiting examples.

EXAMPLES

Example 1

Preparation of the Crystalline Tetrahydrofuran Solvate of Darunavir

Darunavir tetrahydrofuran solvate of the present invention was prepared by dissolving about 1 g of Darunavir ethanolate in 5 ml of a tetrahydrofuran solvent. The solvent was then allowed to evaporate at room temperature (approximately 25° C.) until crystals were formed.

Alternatively, the darunavir tetrahydrofuran solvate of the present invention was prepared by dissolving Darunavir ethanolate in a tetrahydrofuran solvent, followed by the addition of the antisolvent isopropanol (IPA) to induce precipitation of the crystals.

Alternatively, the darunavir tetrahydrofuran solvate of the present invention was prepared by dissolving Darunavir ethanolate in tetrahydrofuran (THF):isopropyl acetate (iPrOAc) at a ratio of 1:2 or tetrahydrofuran (THF):methyl tert-butyl ether (MTBE) at a ratio of 1:2, heating the mixture to 60° C., followed by cooling using an ice-bath to induce crystallization.

Example 2

Characterization of the Crystalline Tetrahydrofuran Solvate of Darunavir

Figure 2:
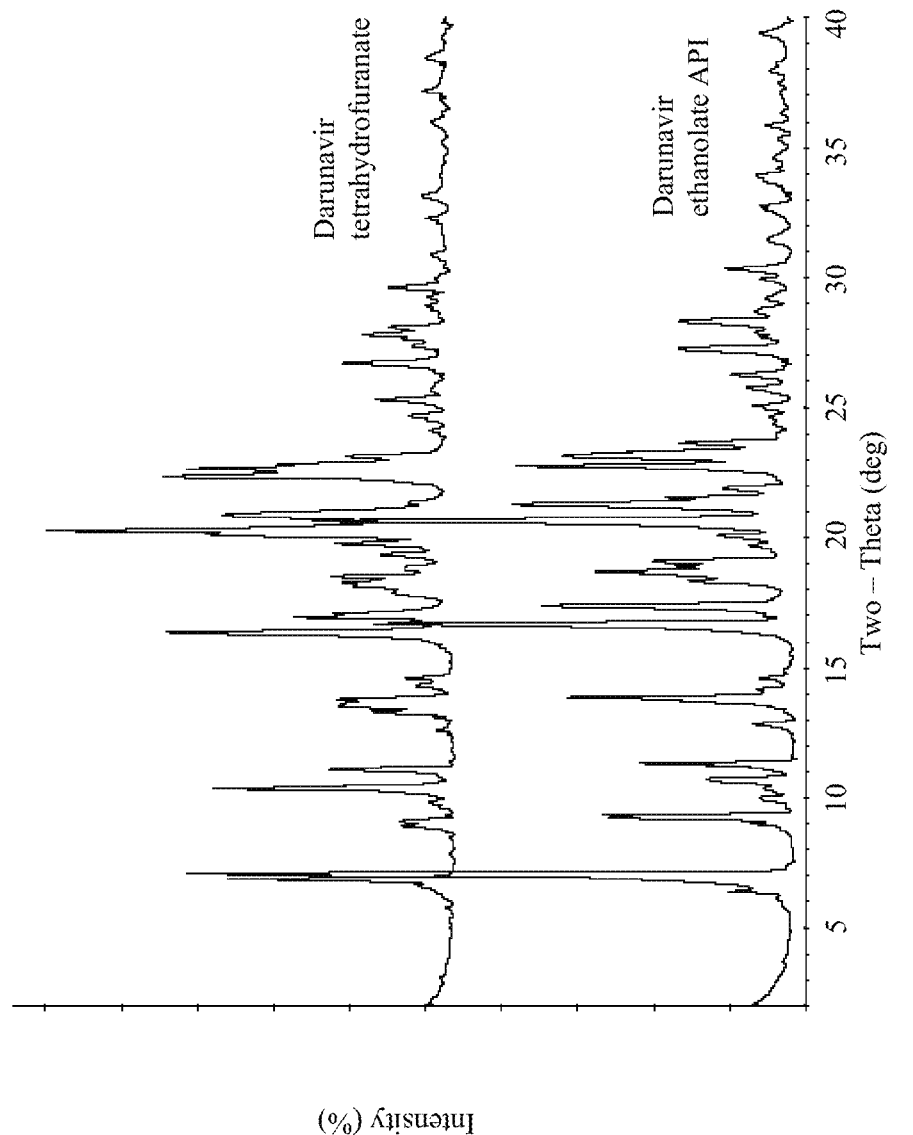
FIG. 2 is a characteristic X-ray diffraction pattern of the crystalline tetrahydrofuran solvate of darunavir in comparison to darunavir ethanolate API.

This new polymorphic form showed an endothermic peak in Differential Scanning Calorimetry (DSC; Mettler Toledo DSC 1; 10° C./min) at ~95° C. X-ray powder diffraction (XRPD; Rigaku D/MAX 2200, CuKα, 40 kV, 40 mA, DivSlit 1 deg, DivH.L.Slit 10 mm, SctSlit 1 deg, RecSlit 0.3 mm, 10 deg/min) shows unique characteristic peaks (FIG. 1; Table 1). The X-ray diffraction pattern of the tetrahydrofuran solvate of darunavir of the present invention has a unique fingerprint which differs from the X-ray diffraction pattern of darunavir ethanolate API (FIG. 2). The XRPD and DSC spectra remained unchanged even after storage at 25° C. for 2 weeks, thus indicating crystal stability.

TABLE 1

X-ray diffraction peaks of darunavir tetrahydrofuran solvate

| 2-theta | d-spacing [Å] | Width at half height | Relative intensity* (%) |
|---|---|---|---|
| 6.898 | 12.8032 | 0.213 | 39.7 |
| 9.142 | 9.6656 | 0.153 | 26.8 |
| 10.340 | 8.5484 | 0.338 | 19.9 |
| 10.980 | 8.0518 | 0.253 | 51.8 |
| 13.579 | 6.5155 | 0.223 | 38.2 |
| 16.060 | 5.5143 | 0.377 | 32.3 |
| 16.398 | 5.4013 | 0.232 | 98.9 |
| 17.123 | 5.1744 | 0.174 | 54.1 |
| 18.380 | 4.8231 | 0.440 | 35.8 |
| 19.824 | 4.4749 | 0.512 | 26.8 |
| 20.221 | 4.3879 | 0.337 | 52.8 |
| 20.920 | 4.2428 | 0.411 | 54.2 |
| 22.381 | 3.9691 | 0.563 | 86.4 |
| 22.801 | 3.8970 | 0.325 | 100.0 |
| 23.160 | 3.8374 | 0.427 | 33.0 |
| 27.740 | 3.2133 | 0.528 | 19.2 |
| 28.041 | 3.1795 | 0.528 | 18.9 |

*Relative intensities may vary among samples.

Figure 3:
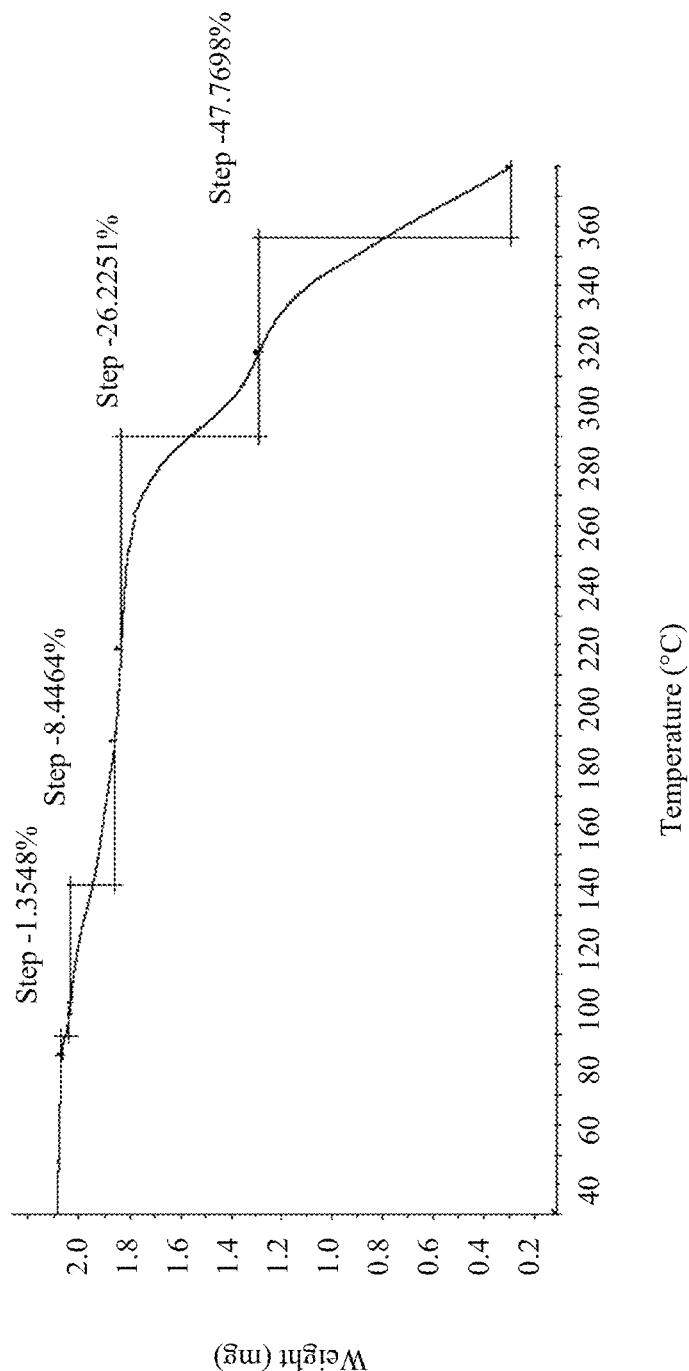
FIG. 3 is a characteristic Thermogravimetric analysis (TGA) of the crystalline tetrahydrofuran solvate of darunavir.
Figure 4A:
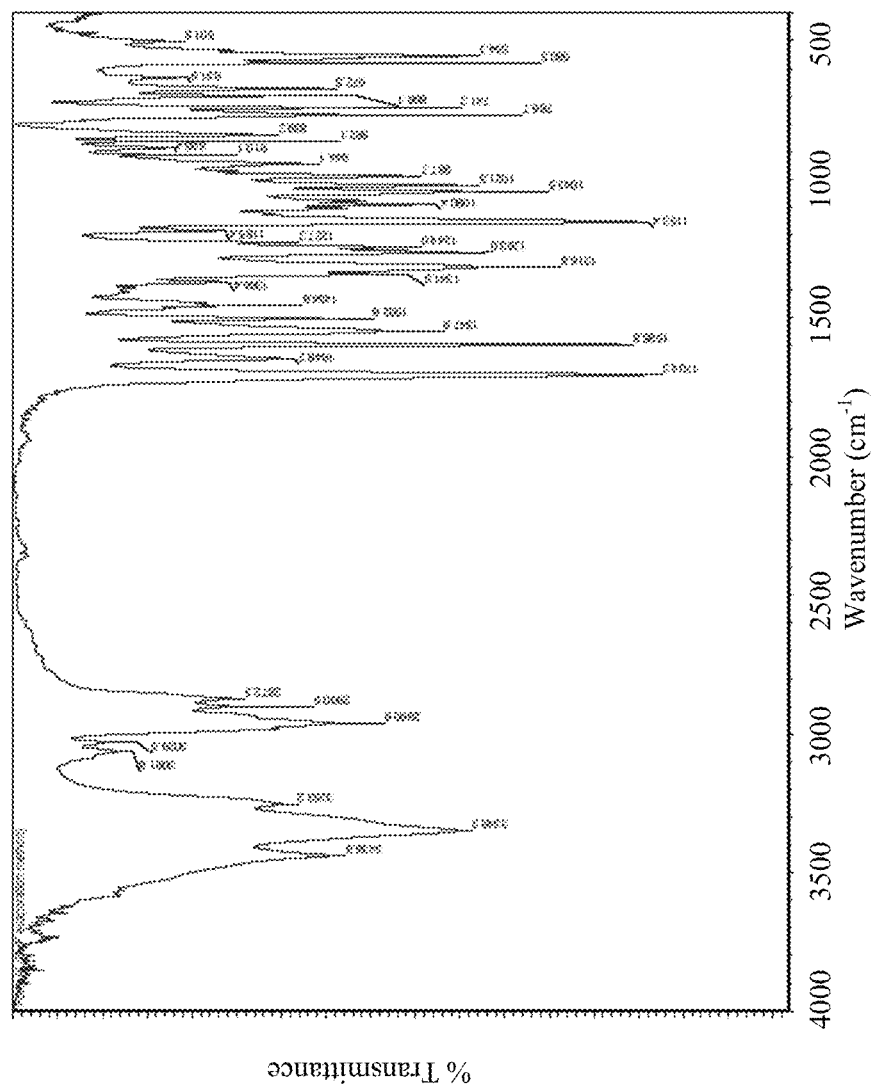
FIG. 4 is a characteristic IR spectrum of the crystalline tetrahydrofuran solvate of darunavir (4A) in comparison to darunavir ethanolate API (4B).
Figure 4B:
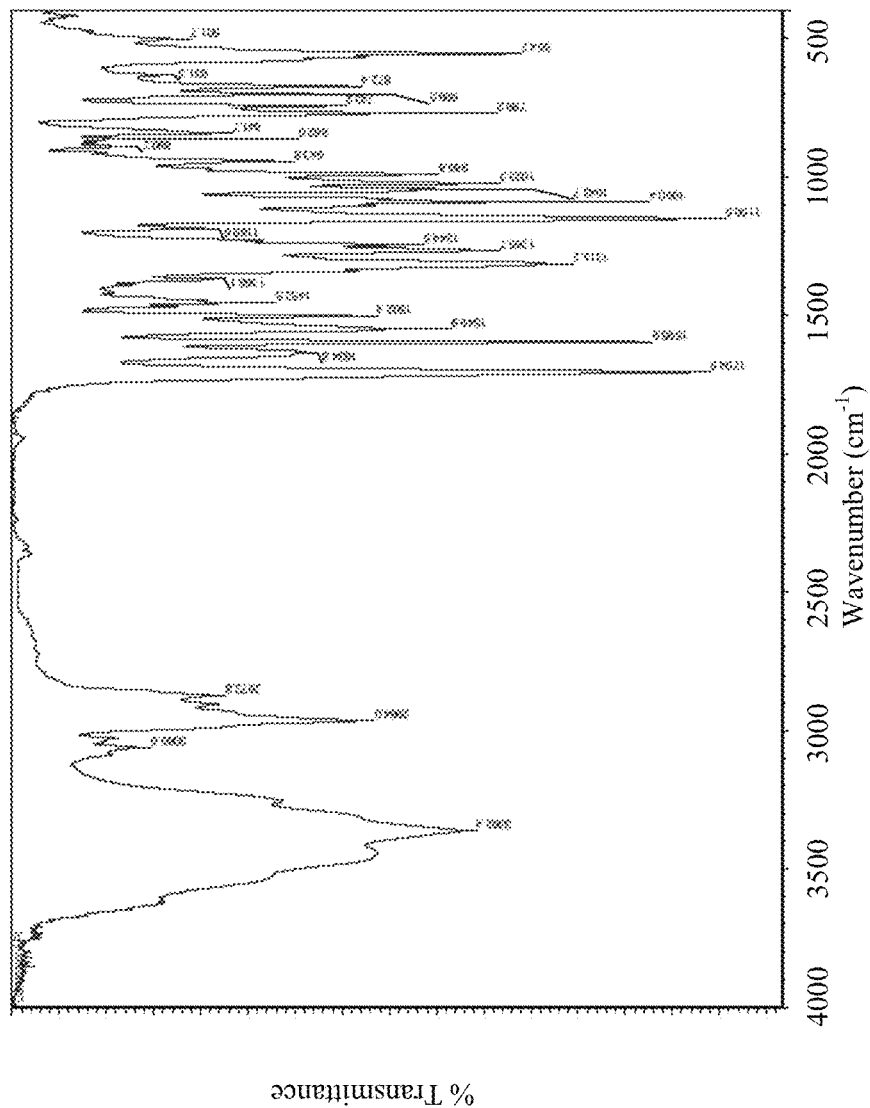
Figure 5:
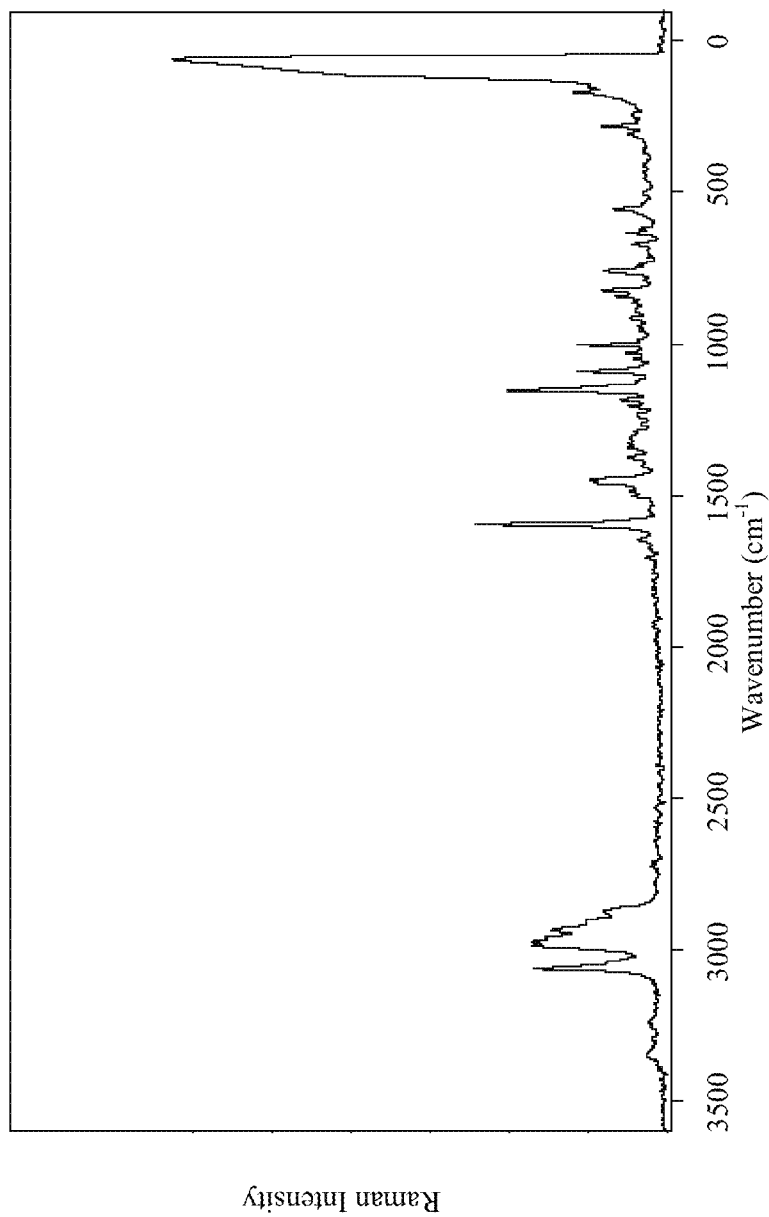
FIG. 5 is a characteristic Raman spectrum of the crystalline tetrahydrofuran solvate of darunavir.
Figure 6:
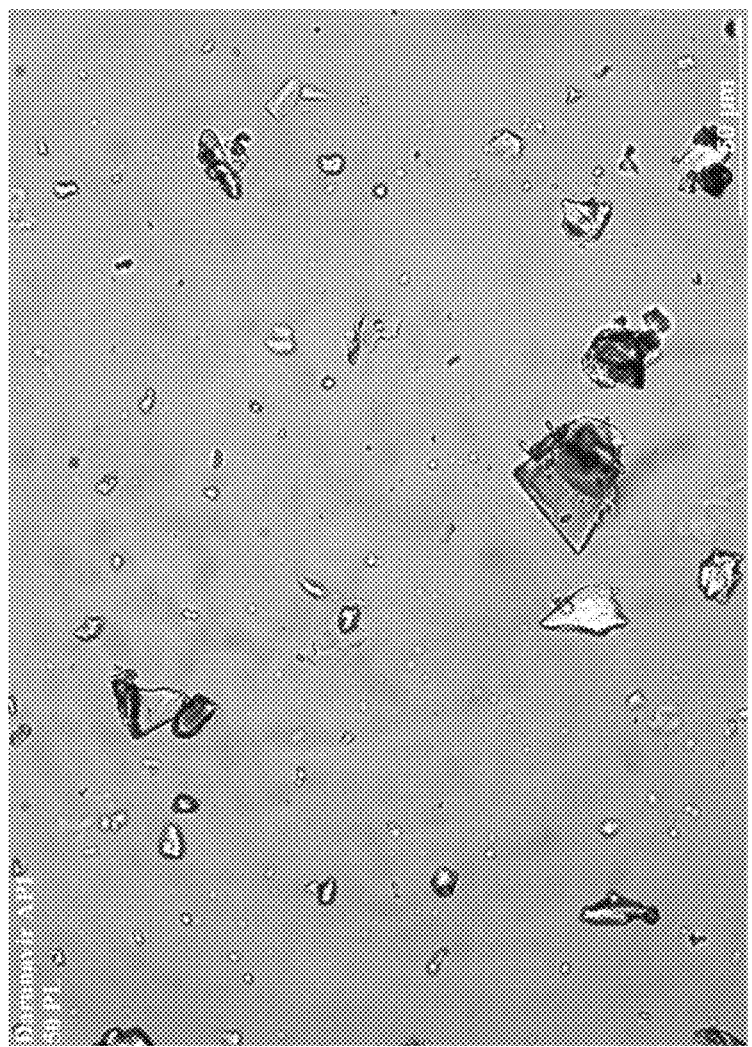
FIG. 6 is a polarized light micrograph of the crystalline tetrahydrofuran solvate of darunavir.

Thermogravimetric analysis (TGA; Mettler Toledo TGA/DSC 1100, 10° C./min) showed a weight loss of approximately 1.3% at temperatures of 60-100° C. and another weight loss of approximately 8.5% at temperatures of 100-190° C. (FIG. 3). Infrared (IR) spectroscopy revealed significant differences between the tetrahydrofuran solvate form of the present invention and the known ethanolate form, particularly at the alcohol region (3100-3400 cm$^{-1}$; FIGS. 4A and 4B, respectively). The Raman spectrum is shown in FIG. 5. The characteristic Raman peaks of the darunavir tetrahydrofuran solvate of the present invention appear at about 62, 171, 283, 555, 636, 672, 760, 824, 1004, 1091, 1155, 1376, 1448, 1596, 1647, 2871, 2937, 2974, and 3064 cm$^{-1}$. Differences in the Raman spectra between the tetrahydrofuran solvate form of the present invention and the known ethanolate form of darunavir appear at least at the following wavenumbers (cm$^{-1}$): 2871, 1647, 1376 and 1155. Polarized light microscopy of the crystals revealed small birefringent plates (Nikon LV100POL equipped with 5 megapixel CCD, Physical lens 50×; FIG. 6). The bulk density of the darunavir tetrahydrofuran solvate of the present invention is 0.431±0.007 g/ml.

About 10 mg of the tetrahydrofuran solvate form of the present invention were used to test the hygroscopicity (DVS) from 0% to 90% according to the details on Table 2.

TABLE 2

Parameters for hygroscopicity measurements (dynamic vapor sorption; DVS)

| Stage number | Stage type | dm/dt (%/min) | Start PP (%) | Stop PP (%) | Temp (° C.) |
|---|---|---|---|---|---|
| 1 | dm/dt | 0.002 | 0.0 | 0.0 | 25.0 |
| 2 | dm/dt | 0.002 | 10.0 | 10.0 | 25.0 |
| 3 | dm/dt | 0.002 | 20.0 | 20.0 | 25.0 |
| 4 | dm/dt | 0.002 | 30.0 | 30.0 | 25.0 |
| 5 | dm/dt | 0.002 | 40.0 | 40.0 | 25.0 |
| 6 | dm/dt | 0.002 | 50.0 | 50.0 | 25.0 |
| 7 | dm/dt | 0.002 | 60.0 | 60.0 | 25.0 |
| 8 | dm/dt | 0.002 | 70.0 | 70.0 | 25.0 |
| 9 | dm/dt | 0.002 | 80.0 | 80.0 | 25.0 |
| 10 | dm/dt | 0.002 | 90.0 | 90.0 | 25.0 |
| 11 | dm/dt | 0.002 | 80.0 | 80.0 | 25.0 |
| 12 | dm/dt | 0.002 | 70.0 | 70.0 | 25.0 |
| 13 | dm/dt | 0.002 | 60.0 | 60.0 | 25.0 |
| 14 | dm/dt | 0.002 | 50.0 | 50.0 | 25.0 |
| 15 | dm/dt | 0.002 | 40.0 | 40.0 | 25.0 |
| 16 | dm/dt | 0.002 | 30.0 | 30.0 | 25.0 |
| 17 | dm/dt | 0.002 | 20.0 | 20.0 | 25.0 |
| 18 | dm/dt | 0.002 | 10.0 | 10.0 | 25.0 |
| 19 | dm/dt | 0.002 | 0.0 | 0.0 | 25.0 |

Figure 7:
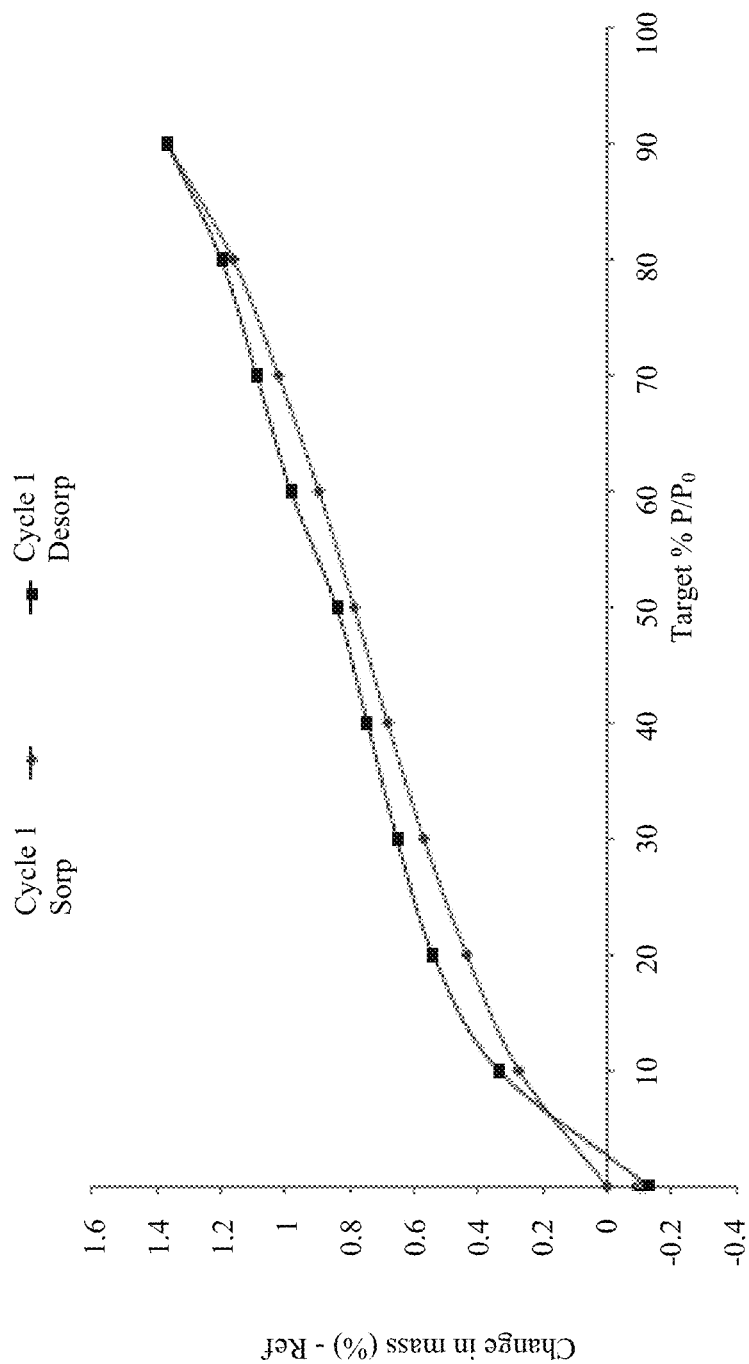
FIG. 7 is a dynamic vapor sorption (DVS) isotherm plot of the crystalline tetrahydrofuran solvate of darunavir. Sorption is represented by diamonds and desorption is represented by squares.

The tetrahydrofuran solvate form of the present invention was found to be slightly hygroscopic (1.366% weight gain from 0% to 90%; FIG. 7).

The tetrahydrofuran solvate of darunavir of the present invention was further evaluated for its chemical stability. The results are summarized in Table 3. Specifically, about 3 mg of the compound were weighed accurately into a 20 ml clear glass vial and stored under the following conditions: 40° C., 60° C., 40° C./RH 75%, 60° C./RH 75%, and light (25° C.), for 2 weeks. A sample stored at −20° C. was used as control. A slight increase in Total Related Substances (TRS) was found at 40° C. which was more significant at 60° C. and 60° C./75% RH. In contrast, no increase was observed when the tetrahydrofuran solvate was stored under exposure to light at 25° C., both at the end of 1$^{st}$ and 2$^{nd}$ week. Additionally, no change was observed in the physical appearance at the end of the 1$^{st}$ and 2$^{nd}$ week for samples stored at 40° C., 40° C./RH 75% and 25° C. under light. Samples that were stored at 60° C. and 60° C./75% RH were found stuck to the glass vial.

TABLE 3

Solid stability of darunavir tetrahydrofuran solvate at 40° C., 60° C., 40° C./75% RH, 60° C./75% RH and under exposure to light for 7 days and 14 days

| Condition | Time | Sample number | Weight (mg) | Appearance | TRS % | Remaining % |
|---|---|---|---|---|---|---|
| −20° C. | 7 d | 1 | 2.446 | No change | 3.54 | — |
|  |  | 2 | 2.547 | No change | 3.52 |  |
|  | 14 d | 1 | 1.935 | No change | 3.44 | — |
|  |  | 2 | 3.040 | No change | 3.53 |  |
| 40° C. | 7 d | 1 | 2.469 | No change | 4.11 | 99.83 |
|  |  | 2 | 2.775 | No change | 4.02 |  |
|  | 14 d | 1 | 2.628 | No change | 4.08 | 99.64 |
|  |  | 2 | 3.422 | No change | 4.15 |  |
| 60° C. | 7 d | 1 | 2.903 | Stuck | 6.25 | 97.24 |
|  |  | 2 | 2.222 | Stuck | 5.70 |  |
|  | 14 d | 1 | 3.166 | Stuck | 8.88 | 94.12 |
|  |  | 2 | 2.512 | Stuck | 9.37 |  |
| 40° C./ 75% RH | 7 d | 1 | 2.532 | No change | 2.84 | 100.77 |
|  |  | 2 | 2.824 | No change | 3.17 |  |
|  | 14 d | 1 | 2.227 | No change | 2.82 | 101.52 |
|  |  | 2 | 2.681 | No change | 2.65 |  |
| 60° C./ 75% RH | 7 d | 1 | 2.479 | Stuck | 5.05 | 97.84 |
|  |  | 2 | 2.650 | Stuck | 4.17 |  |
|  | 14 d | 1 | 2.869 | Stuck | 4.34 | 98.59 |
|  |  | 2 | 2.856 | Stuck | 5.19 |  |
| light | 7 d | 1 | 3.002 | No change | 3.56 | 100.02 |
|  |  | 2 | 2.859 | No change | 3.64 |  |
|  | 14 d | 1 | 2.345 | No change | 3.63 | 100.78 |
|  |  | 2 | 3.012 | No change | 3.57 |  |

Figure 8:
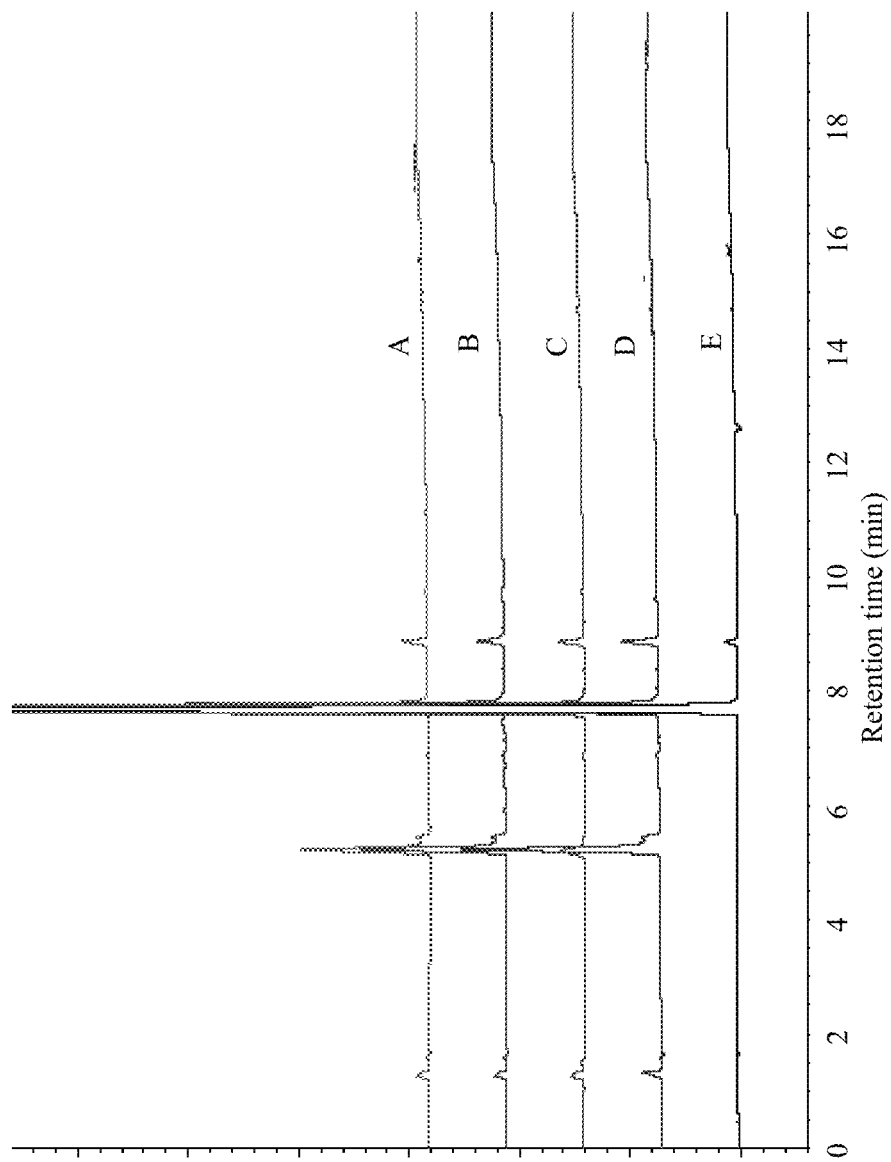
FIG. 8 are HPLC chromatograms of the crystalline dimethylsulfoxide solvate of darunavir (panel A), the crystalline tetrahydrofuran solvate of darunavir (panel B), the amorphous darunavir of the present invention (panel C), and darunavir ethanolate API (panel D) slurry in pH 1.2 buffer. Panel E is a chromatogram of darunavir ethanolate API standard solution (STD).

The aqueous solubility of the tetrahydrofuran solvate of darunavir of the present invention was measured. Specifically, about 10 mg of the compound was accurately weighed into a 4 ml clear glass vial followed by the addition of 2.5 ml buffer (at different pH) to the vial. The vial was then mounted on a Thermomixer and was kept shaking for 24 hours at 25° C. The solution was filtered through 0.45 μm PTFE filter. The pH value and concentration of the filtrate were checked by pH meter and HPLC (Agilent 1200; Column: Zorbax SB C18, 4.6 mm×150 mm ID×5 μm; Profile of mobile phase: t=0 water 70, ACN 30; t=15, 20 water 0, ACN 100; Column temperature 30° C.; Mobile rate 1.0 mL/min; Detector wavelength 265 nm; The typical retention time of Darunavir is 7.7 min), respectively. The results are summarized in Table 4 and FIG. 8 panel B.

TABLE 4

Solubility results of darunavir tetrahydrofuran solvate in aqueous buffers

| Testing media | Solubility (mg/ml) | Appearance | Final pH |
|---|---|---|---|
| water | 0.27 | Many particles | 5.664 |
| pH 1.2 | 1.47* | Many particles | 1.197 |
| pH 4.5 | 0.27 | Many particles | 4.508 |
| pH 6.8 | 0.24 | Many particles | 6.789 |
| pH 7.4 | 0.23 | Many particles | 7.431 |

*degraded

Example 3

Preparation of the Crystalline Dimethylsulfoxide Solvate of Darunavir

Darunavir dimethylsulfoxide solvate of the present invention was prepared by dissolving Darunavir ethanolate in dimethylsulfoxide at 60° C. followed by cooling using an ice-bath to induce crystallization.

Alternatively, the darunavir dimethylsulfoxide solvate of the present invention was prepared by dissolving about 1 g of Darunavir ethanolate in 2.5 ml dimethylsulfoxide at 80° C. Water (10 ml) was then added to induce crystallization.

Alternatively, the darunavir dimethylsulfoxide solvate of the present invention was prepared by dissolving Darunavir ethanolate in dimethylsulfoxide followed by the addition of the antisolvent isopropanol (IPA) to induce precipitation of the crystals.

Alternatively, the darunavir dimethylsulfoxide solvate of the present invention was prepared by dissolving Darunavir ethanolate in either one of the following solvent mixtures: dimethylsulfoxide (DMSO):methanol (MeOH) at a ratio of 1:10, dimethylsulfoxide (DMSO):toluene at a ratio of 1:10 or dimethylsulfoxide (DMSO):ethanol (EtOH) at a ratio of 1:10 at 60° C. The mixtures were then allowed to evaporate until crystals were formed.

Example 4

Characterization of the Crystalline Dimethylsulfoxide Solvate of Darunavir

Figure 9:
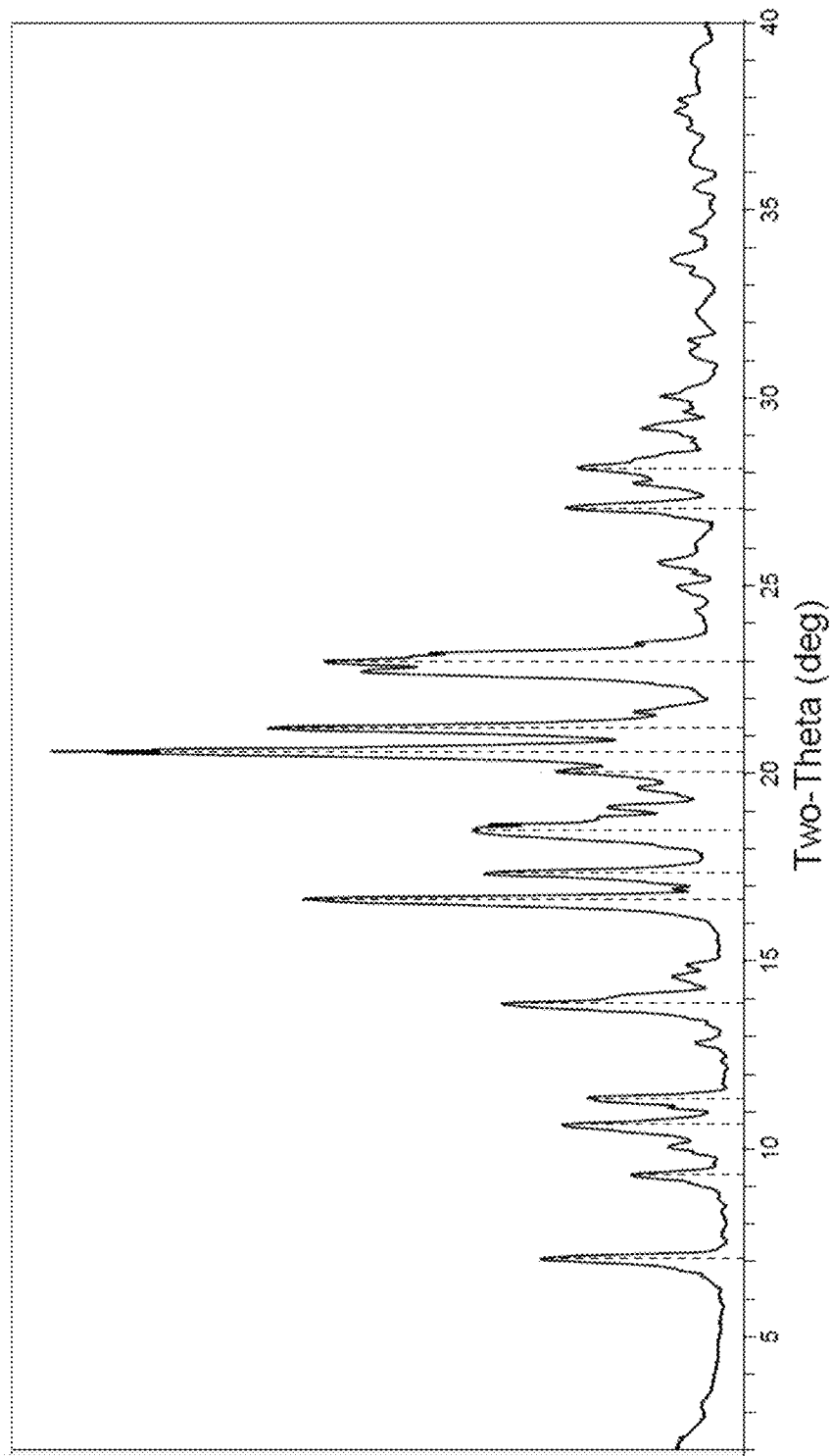
FIG. 9 is a characteristic X-ray diffraction pattern of the crystalline dimethylsulfoxide solvate of darunavir.
Figure 10:
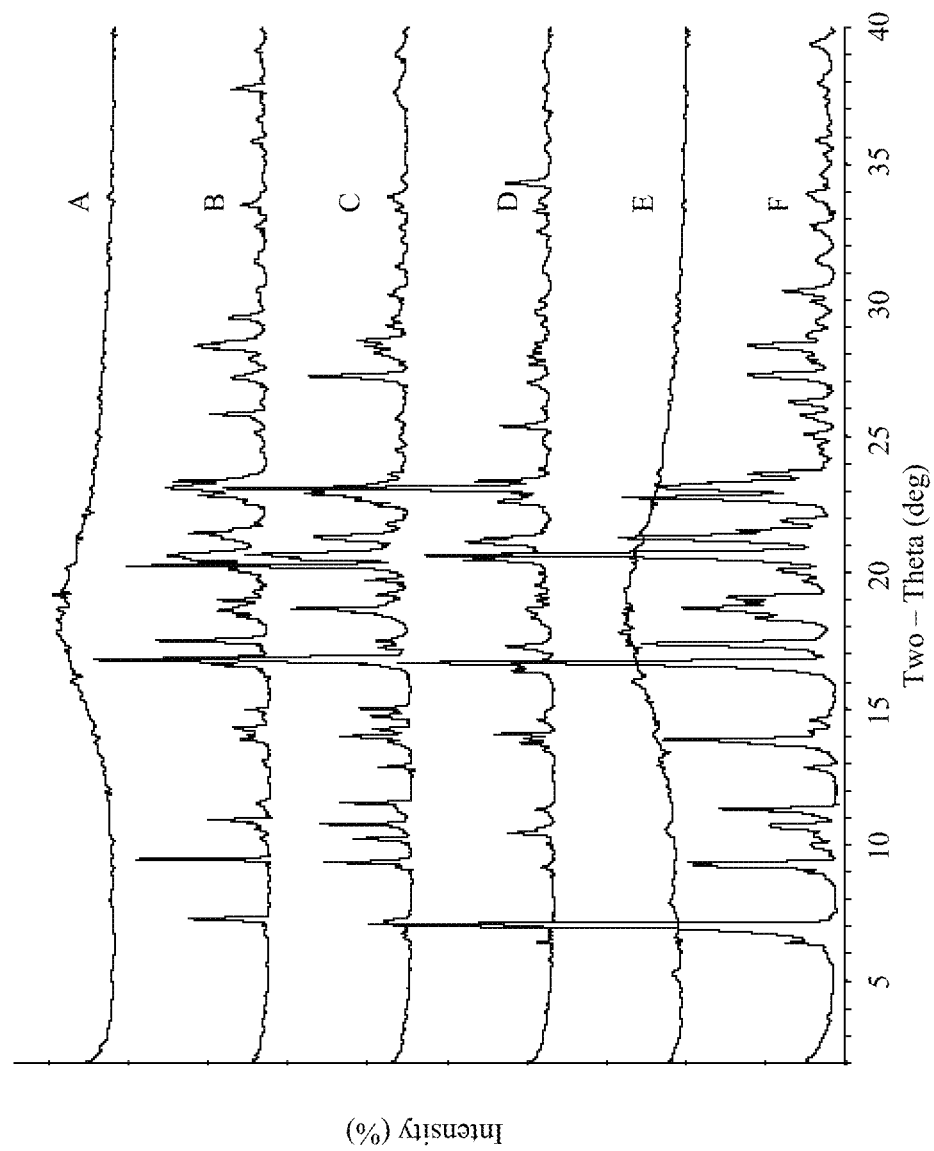
FIG. 10 are characteristic X-ray diffraction patterns of the crystalline dimethylsulfoxide solvate of darunavir (panels B-D) in comparison to darunavir ethanolate API (panel F) and the amorphous darunavir form (panels A and E).

The crystalline dimethylsulfoxide solvate of darunavir showed an endothermic peak at ~115° C. using Differential Scanning Calorimetry. The X-ray powder diffraction of the darunavir dimethylsulfoxide solvate of the present invention is presented in FIG. 9 and Table 5. The X-ray diffraction pattern shows a unique fingerprint (FIG. 10, panels B, C, and D) which differs from the diffraction pattern of the known ethanolate crystalline form (FIG. 10, panel F). The XRPD and DSC spectra remained unchanged even after storage at 25° C. for 2 weeks indicating crystal stability.

TABLE 5

X-ray diffraction peaks of darunavir dimethylsulfoxide solvate

| 2-theta | d-spacing [Å] | Width at half height | Relative intensity* (%) |
|---|---|---|---|
| 7.080 | 12.4755 | 0.277 | 29.5 |
| 9.318 | 9.4832 | 0.247 | 16.2 |
| 10.640 | 8.3078 | 0.461 | 26.3 |
| 11.361 | 7.7826 | 0.277 | 22.5 |
| 13.878 | 6.3759 | 0.332 | 34.9 |
| 16.640 | 5.3232 | 0.281 | 63.7 |
| 17.340 | 5.1101 | 0.214 | 37.6 |
| 18.500 | 4.7922 | 0.543 | 39.2 |
| 20.060 | 4.4228 | 0.535 | 27.2 |
| 20.580 | 4.3123 | 0.326 | 100.0 |
| 21.200 | 4.1874 | 0.310 | 68.7 |
| 22.999 | 3.8638 | 0.594 | 60.7 |
| 27.060 | 3.2925 | 0.254 | 25.7 |
| 28.140 | 3.1685 | 0.456 | 24.1 |

*Relative intensities may vary among samples.

Figure 11:
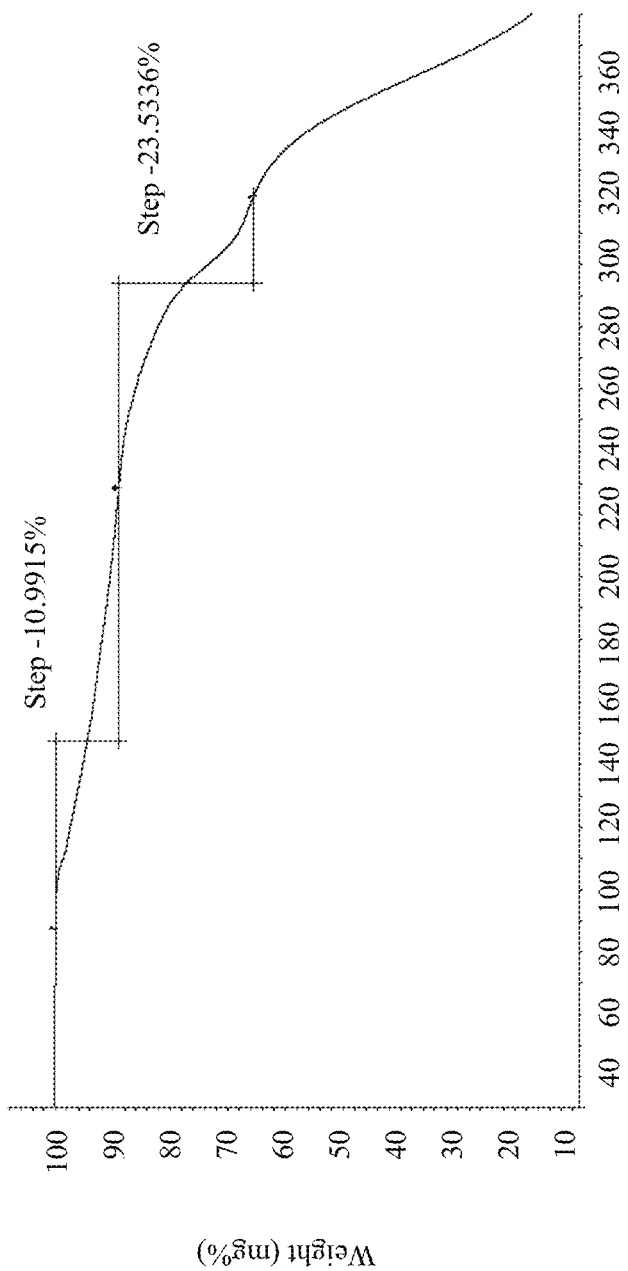
FIG. 11 is a characteristic Thermogravimetric analysis (TGA) of the crystalline dimethylsulfoxide solvate of darunavir.
Figure 12:
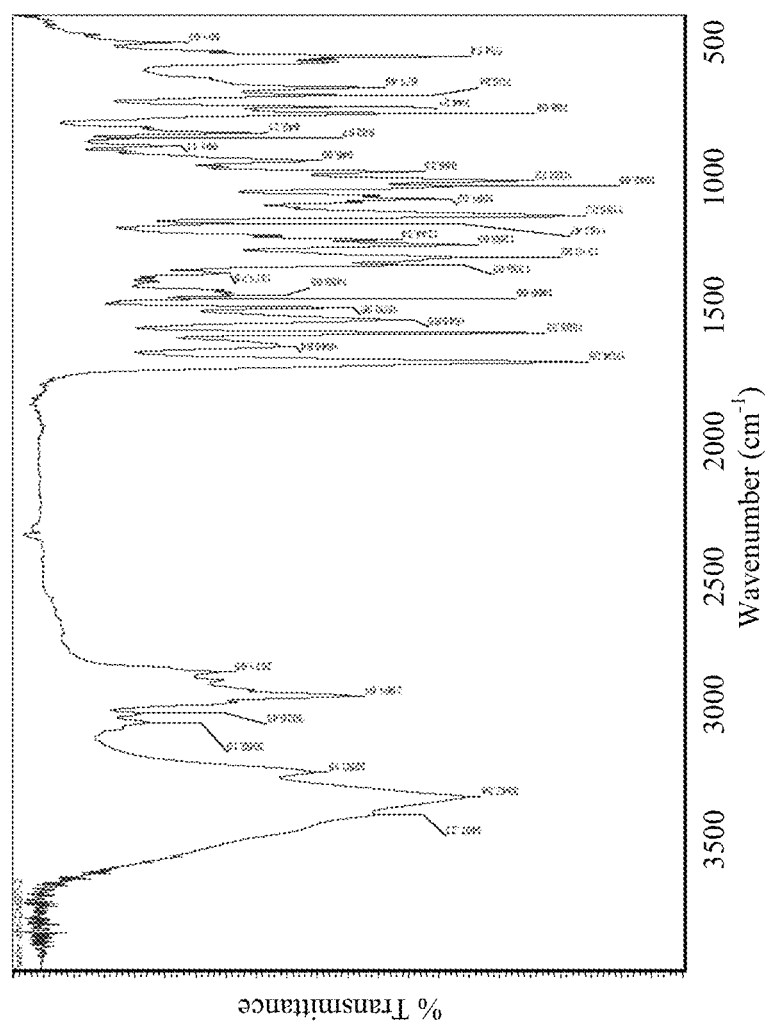
FIG. 12 is a characteristic IR spectrum of the crystalline dimethylsulfoxide solvate of darunavir.
Figure 13:
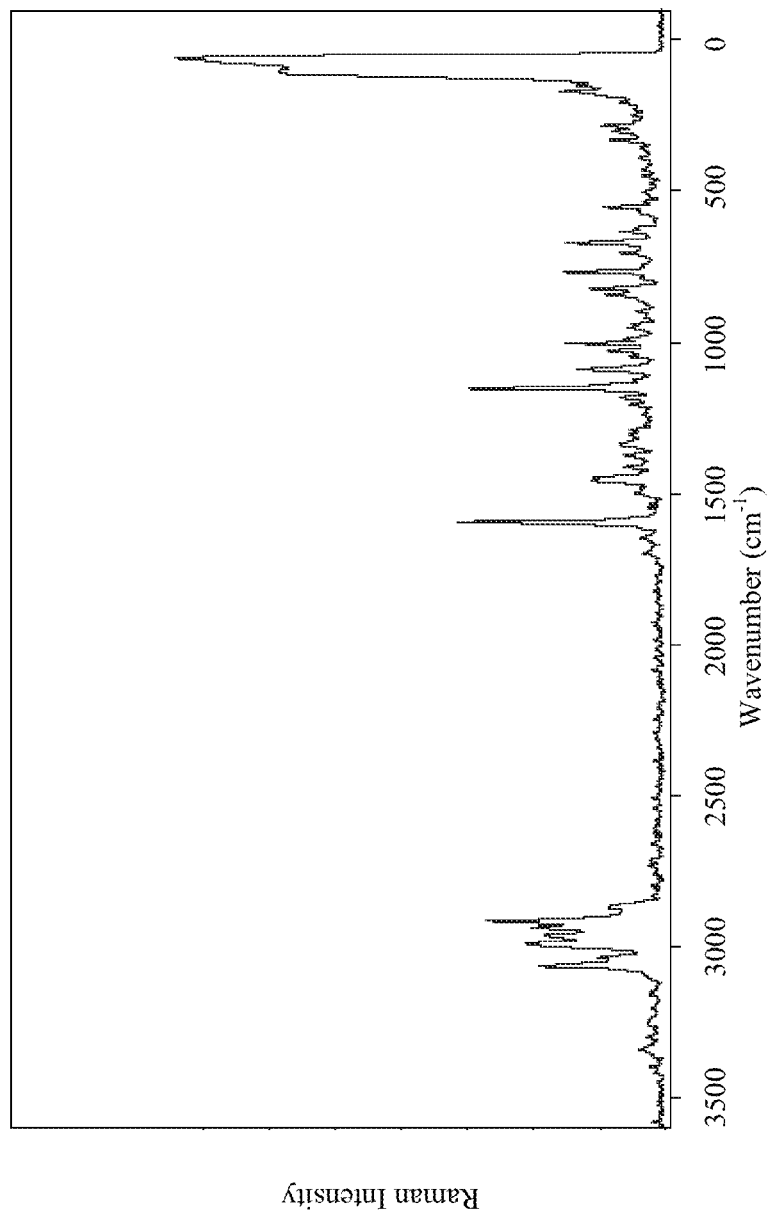
FIG. 13 is a characteristic Raman spectrum of the crystalline dimethylsulfoxide solvate of darunavir.

Thermogravimetric analysis of darunavir dimethylsulfoxide solvate showed a weight loss of approximately 11% at a temperature range of RT-230° C. substantially attributed to the release of solvate molecules (FIG. 11). FIG. 12 shows the Infrared (IR) spectrum of the darunavir dimethylsulfoxide solvate of the present invention which has significant differences from other known forms of darunavir, particularly at the alcohol region (3100-3400 cm$^{-1}$). The Raman spectrum is shown in FIG. 13. The characteristic Raman peaks of the darunavir dimethylsulfoxide solvate of the present invention appear at about 108, 172, 284, 333, 391, 555, 673, 707, 768, 824, 954, 1004, 1031, 1081, 1155, 1184, 1208, 1291, 1341, 1375, 1414, 1459, 1595, 1649, 1700, 2871, 2915, 2937, 2962, 2989, 3064, and 3340 cm$^{-1}$. Differences in the Raman intensity between the dimethylsulfoxide solvate form of the present invention and the known ethanolate form of darunavir appear at least at the following wavenumbers (cm$^{-1}$): 3340, 2915, 2871, 1700, 1649, 1414, 1375, 1341, 1291, 1208, 1184, 1031, 954, 707, 391, 333, and 108. The bulk density of the darunavir dimethylsulfoxide solvate of the present invention is 0.472±0.008 g/ml, approximately 26% denser when compared to the bulk density (0.374±0.009 g/mL) of the known ethanolate form.

Figure 14:
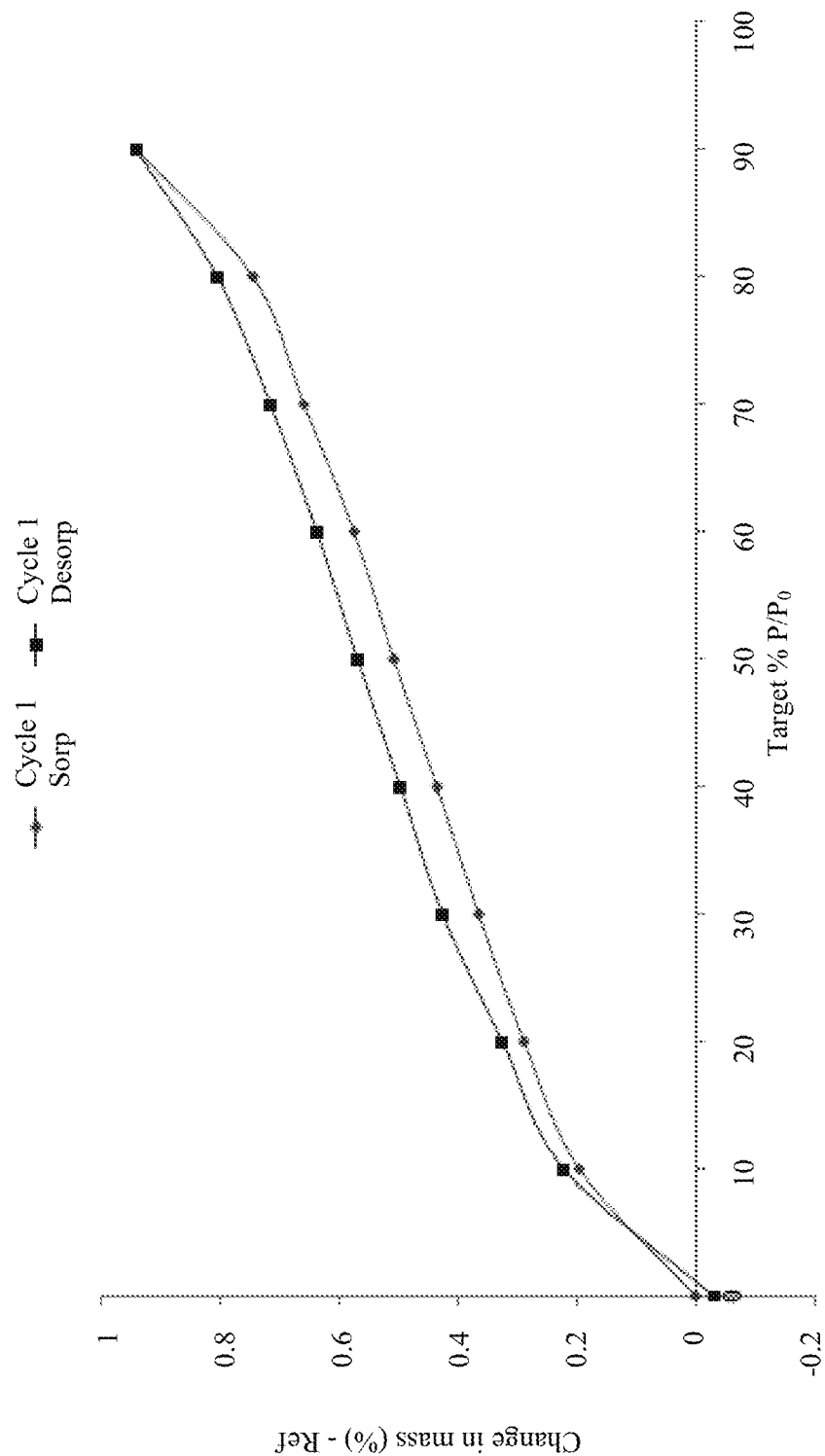
FIG. 14 is a dynamic vapor sorption (DVS) isotherm plot of the crystalline dimethylsulfoxide solvate of darunavir. Sorption is represented by diamonds and desorption is represented by squares.

About 10 mg of the dimethylsulfoxide solvate form of the present invention were used to test the hygroscopicity (DVS) from 0% to 90% according to the details on Table 2 hereinabove. The dimethylsulfoxide solvate form of the present invention was found to be only slightly hygroscopic (0.9431% weight gain from 0% to 90%; FIG. 14).

The dimethylsulfoxide solvate of darunavir of the present invention was further evaluated for its chemical stability. The results are summarized in Table 6. Specifically, about 3 mg of the compound was accurately weighed into a 20 ml clear glass vial and stored under the following conditions: 40° C., 60° C., 40° C./RH 75%, 60° C./RH 75%, and light (25° C.), for 2 weeks. A sample stored at −20° C. was used as control. No significant drop in recovery values or increase in TRS was observed at 40° C., 40° C./75% RH and under exposure to light at 25° C., while a slight increase was found at 60° C. and 60° C./75% RH. The extent of degradation of the dimethylsulfoxide solvate of darunavir was less than 50% in comparison to the known ethanolate form, under the accelerated test conditions (60° C. and 60° C./75% RH). Additionally, no change was observed in the physical appearance at the end of the 1$^{st}$ and 2$^{nd}$ week for samples stored at 40° C., 40° C./RH 75% and 25° C. under light.

TABLE 6

Solid stability of darunavir dimethylsulfoxide solvate at 40° C., 60° C., 40° C./75% RH, 60° C./75% RH and under light exposure for 7 days and 14 days

| Condition | Time | Sample number | Weight (mg) | Appearance | TRS % | Remaining % |
|---|---|---|---|---|---|---|
| −20° C. | 7 d | 1 | 2.881 | No change | 1.22 | — |
| | | 2 | 2.684 | No change | 1.22 | |
| | 14 d | 1 | 1.932 | No change | 1.22 | — |
| | | 2 | 3.244 | No change | 1.27 | |
| 40° C. | 7 d | 1 | 2.226 | No change | 1.21 | 99.21 |
| | | 2 | 2.853 | No change | 1.21 | |
| | 14 d | 1 | 3.557 | No change | 1.27 | 100.19 |
| | | 2 | 2.825 | No change | 1.27 | |
| 60° C. | 7 d | 1 | 2.957 | Stuck | 1.43 | 99.95 |
| | | 2 | 2.767 | Stuck | 1.29 | |
| | 14 d | 1 | 2.755 | Stuck | 2.07 | 99.91 |
| | | 2 | 3.175 | Stuck | 2.12 | |
| 40° C./ 75% RH | 7 d | 1 | 2.534 | No change | 1.22 | 99.54 |
| | | 2 | 2.786 | No change | 1.24 | |
| | 14 d | 1 | 2.639 | No change | 1.23 | 100.31 |
| | | 2 | 2.640 | No change | 1.27 | |
| 60° C./ 75% RH | 7 d | 1 | 2.129 | Stuck | 2.09 | 99.01 |
| | | 2 | 2.791 | Stuck | 2.08 | |
| | 14 d | 1 | 3.352 | Stuck | 2.04 | 99.85 |
| | | 2 | 2.341 | Stuck | 1.91 | |
| light | 7 d | 1 | 2.228 | No change | 1.29 | 99.59 |
| | | 2 | 2.615 | No change | 1.19 | |
| | 14 d | 1 | 3.633 | No change | 1.22 | 100.12 |
| | | 2 | 2.724 | No change | 1.21 | |

The aqueous solubility of the dimethylsulfoxide solvate of darunavir of the present invention was measured. Specifically, about 10 mg of the compound was accurately weighed into a 4 ml clear glass vial followed by the addition of 2.5 ml buffer (at different pH) to the vial. The vial was then mounted on a Thermomixer and kept shaking for 24 hours at 25° C. The solution was filtered through 0.45 μm PTFE filter. The pH value and concentration of the filtrate were checked by pH meter and HPLC, respectively. The results are summarized in Table 7 and FIG. 8 panel A.

TABLE 7

Solubility results of darunavir dimethylsulfoxide solvate in aqueous buffers

| Testing media | Solubility (mg/ml) | Appearance | Final pH |
|---|---|---|---|
| water | 0.23 | Many particles | 6.001 |
| pH 1.2 | 1.36* | Many particles | 1.236 |
| pH 4.5 | 0.22 | Many particles | 4.486 |
| pH 6.8 | 0.21 | Many particles | 6.785 |
| pH 7.4 | 0.20 | Many particles | 7.437 |

*degraded

Example 5

Preparation and Characterization of Micronized Crystalline Dimethylsulfoxide Solvate of Darunavir Micronized darunavir dimethylsulfoxide solvate was prepared from the non-micronized form by milling using a jet mill (Super Fine Vortex Mill™). Table 8 provides the particle size distribution and surface area, as well as other parameters of micronized and non-micronized darunavir dimethylsulfoxide solvate.

TABLE 8

| Parameter | $D_{10}$ (μm) | $D_{50}$ (μm) | $D_{90}$ (μm) | Specific surface area (m$^2$/g) | Surface weighted mean (μm) | Vol. weighted mean (μm) |
|---|---|---|---|---|---|---|
| Non-micronized | 3.9 | 29.2 | 99.7 | 0.9 | 6.5 | 42.0 |
| Micronized | 1.5 | 3.7 | 7.2 | 2.6 | 2.3 | 4.1 |

Figure 19:
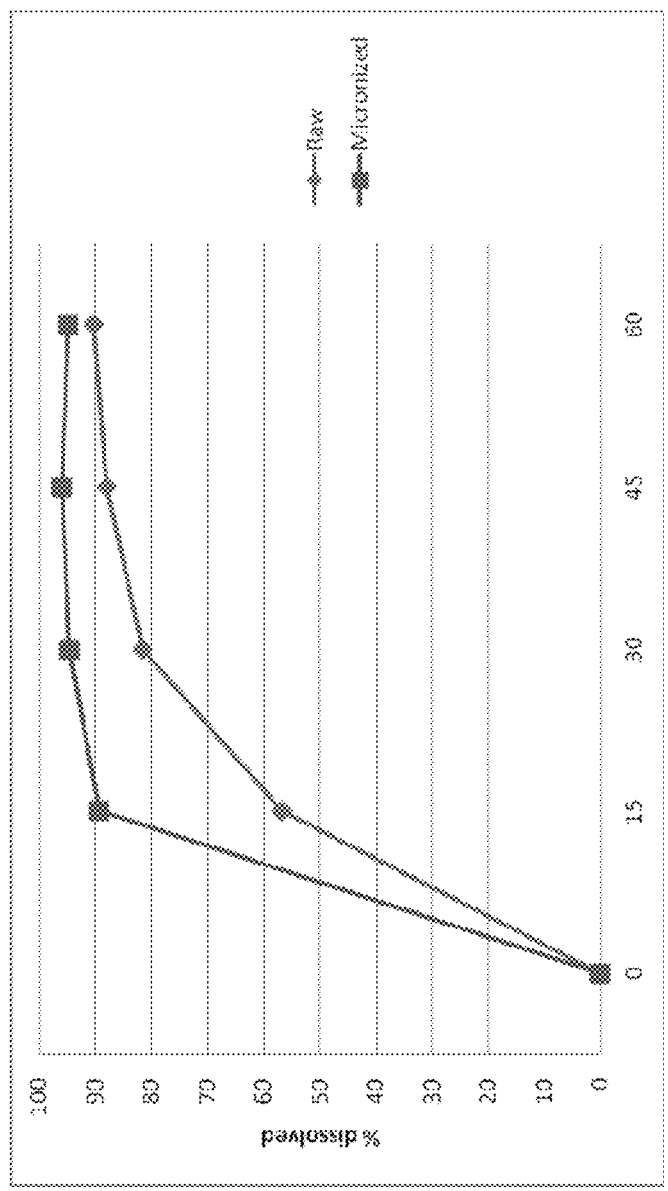
FIG. 19 shows the dissolution profile of raw (non-micronized) Darunavir dimethylsulfoxide solvate (diamonds) and micronized darunavir dimethylsulfoxide solvate (squares).

The dissolution profiles of micronized and non-micronized Darunavir dimethylsulfoxide solvates were compared. 600 mg/vessel of Darunavir DMSO (raw and micronized) were subjected to dissolution testing using the following parameters: USP Apparatus 2 (paddle) at 75 rpm in 900 mL of 2.0% Tween-20 in 0.05M sodium phosphate buffer (pH=3.0) at 37±0.5° C. The results are shown in Table 9 and in FIG. 19.

TABLE 9 dissolution profiles of micronized vs. non-micronized darunavir dimethylsulfoxide solvate

| Time (min) | Dissolution - Micronized (%) | Dissolution - Non-micronized (%) |
|---|---|---|
| 15 | 89.30 | 56.83 |
| 30 | 94.72 | 81.61 |
| 45 | 95.98 | 88.06 |
| 60 | 94.95 | 90.45 |

As seen, the micronized darunavir dimethylsulfoxide solvate has an improved intrinsic dissolution rate s compared with the non-micronized form.

Example 6

Preparation of Amorphous Darunavir

The amorphous darunavir form of the present invention was prepared by slow precipitation from a saturated solution using the following solvent systems: methyl isobutyl ketone (MIBK), isopropyl acetate (iPrOAc), acetonitrile (ACN), dichloromethane (DCM), ethyl acetate (EtOAc) wet and anhydrous, and in the following mixtures of solvents: ACN:Acetone (1:1), at 60° C. with ACN:Toluene (1:6), DCM:MeOH (1:6), Acetone:MeOH (1:6), ACN:MTBE (1:9), Acetone:MTBE (1:9), 2-MeTHF:MeOH (1:8), THF:MeOH (1:9).

Alternatively, the amorphous form was prepared in the following solvent/antisolvent systems: methyl ethyl ketone (MEK)/Methyl tert-butyl ether (MTBE), CH$_2$Cl$_2$/Toluene, acetonitrile (ACN)/H$_2$O, 2-MeTHF/IPA and MIBK/Toluene.

Alternatively, the amorphous form of the present invention was prepared by dissolving about 1 g of Darunavir ethanolate in 1.5 ml CH$_2$Cl$_2$. CH$_2$Cl$_2$ was then evaporated under ambient conditions until a precipitate formed.

Example 7

Characterization of Amorphous Darunavir

The amorphous darunavir of the present invention showed a broad X-ray diffraction peak between 10 and 25 [2θ] characteristic of an amorphous powder (FIG. 10, panels A and E).

Figure 15:
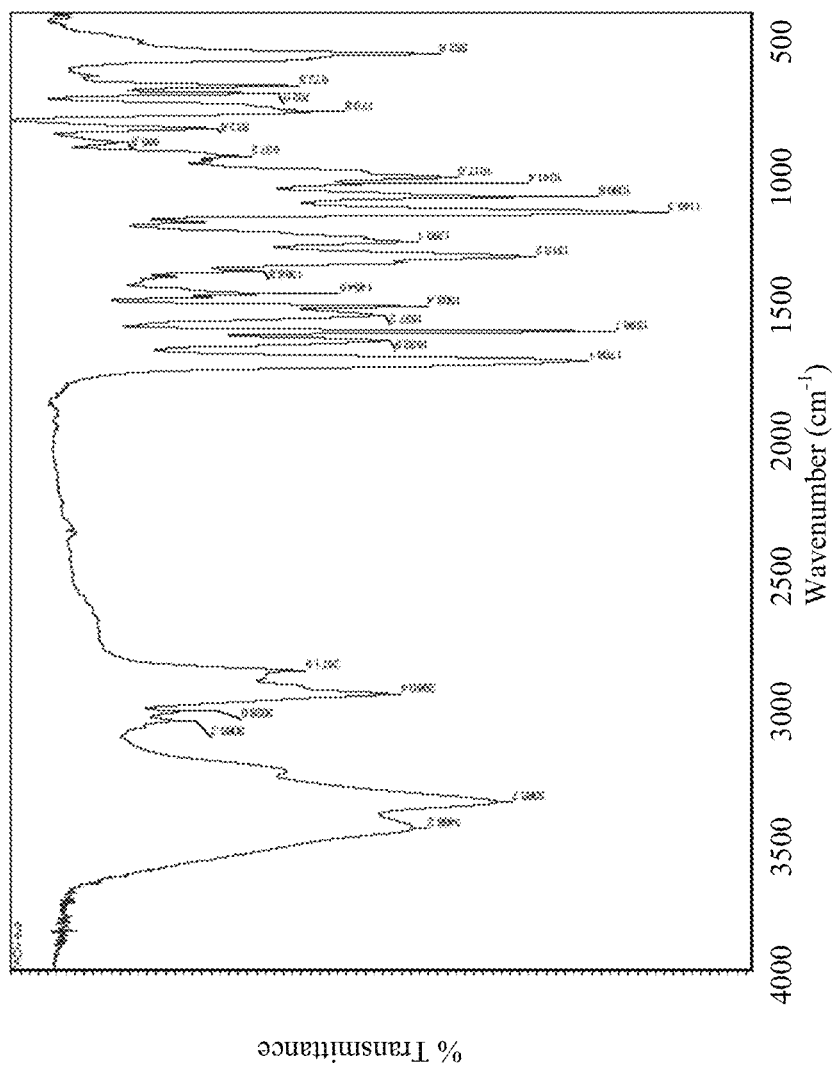
FIG. 15 is a characteristic IR spectrum of the amorphous darunavir of the present invention.

The XRPD remained unchanged even after storage at 25° C. for 2 weeks indicating stability of the amorphous form. The IR spectrum of the amorphous form is shown in FIG. 15. Unique and specific spectral differences between the amorphous form of US 2005/0250845 and the amorphous form of the present invention appear in 2 spectral regions: 1500-1320 cm$^{-1}$ (hereinafter region 1) and 800-500 cm$^{-1}$ (hereinafter region 2).

Figure 16:
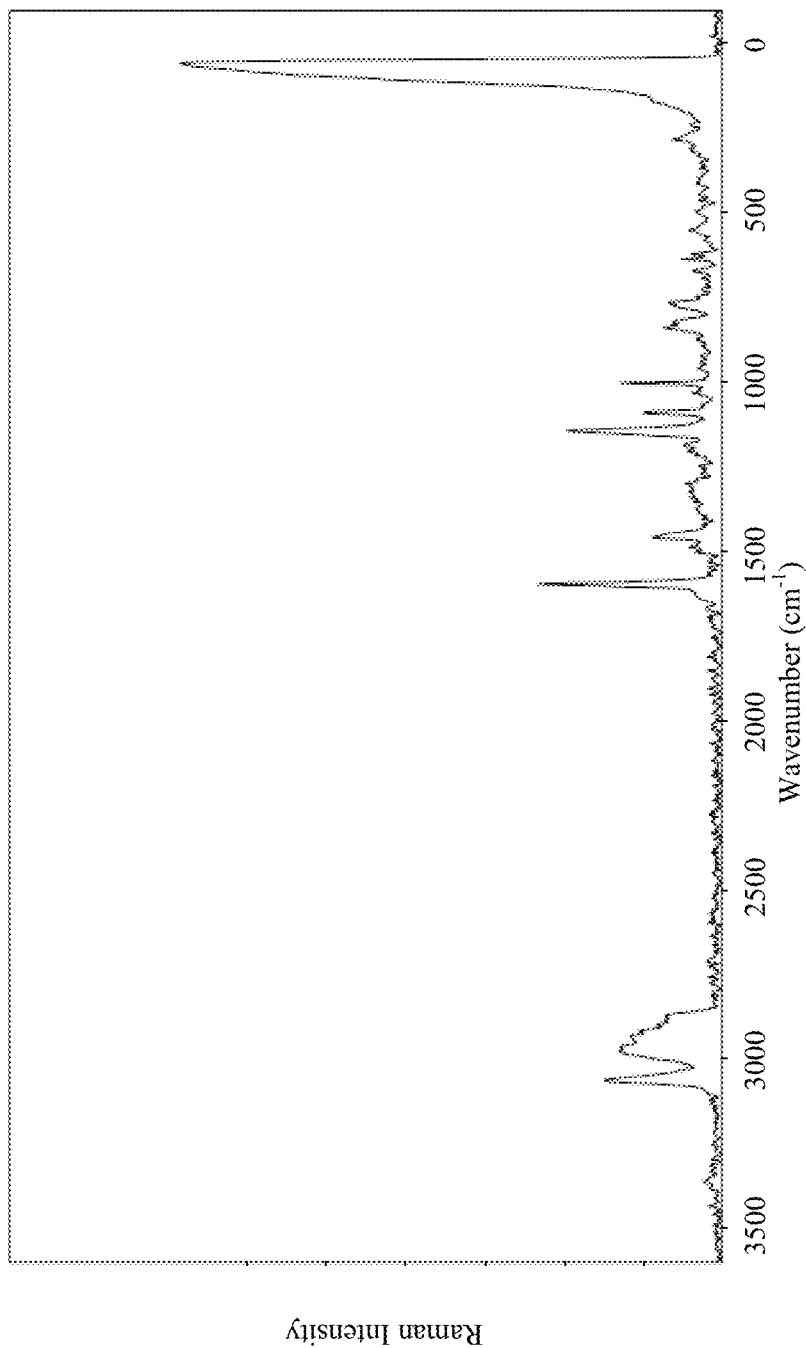
FIG. 16 is a characteristic Raman spectrum of the amorphous darunavir of the present invention.

Specifically, whereas the amorphous form of US 2005/0250845 shows no peaks in region 1, the amorphous form of the present invention is characterized by two single absorption bands at 1454 and 1369 cm$^{-1}$. Additionally, the amorphous form of US 2005/0250845 shows 3 absorption bands at 750, 702 and 672 cm$^{-1}$ in region 2. The amorphous form of the present invention shows 2 additional peaks in this region, at 771 and 553 cm$^{-1}$. The Raman spectrum is shown in FIG. 16. The characteristic Raman peaks of the amorphous darunavir of the present invention appear at about 61, 285, 553, 622, 673, 767, 841, 1004, 1091, 1145, 1459, 1597, 2931, 2966, and 3063 cm$^{-1}$. Differences in the Raman intensity between the amorphous form of the present invention and the known ethanolate form of darunavir appear at least at the following wavenumbers (cm$^{-1}$): 841, 622 and 61. The bulk density of the amorphous darunavir of the present invention is 0.445±0.012 g/ml.

Figure 17:
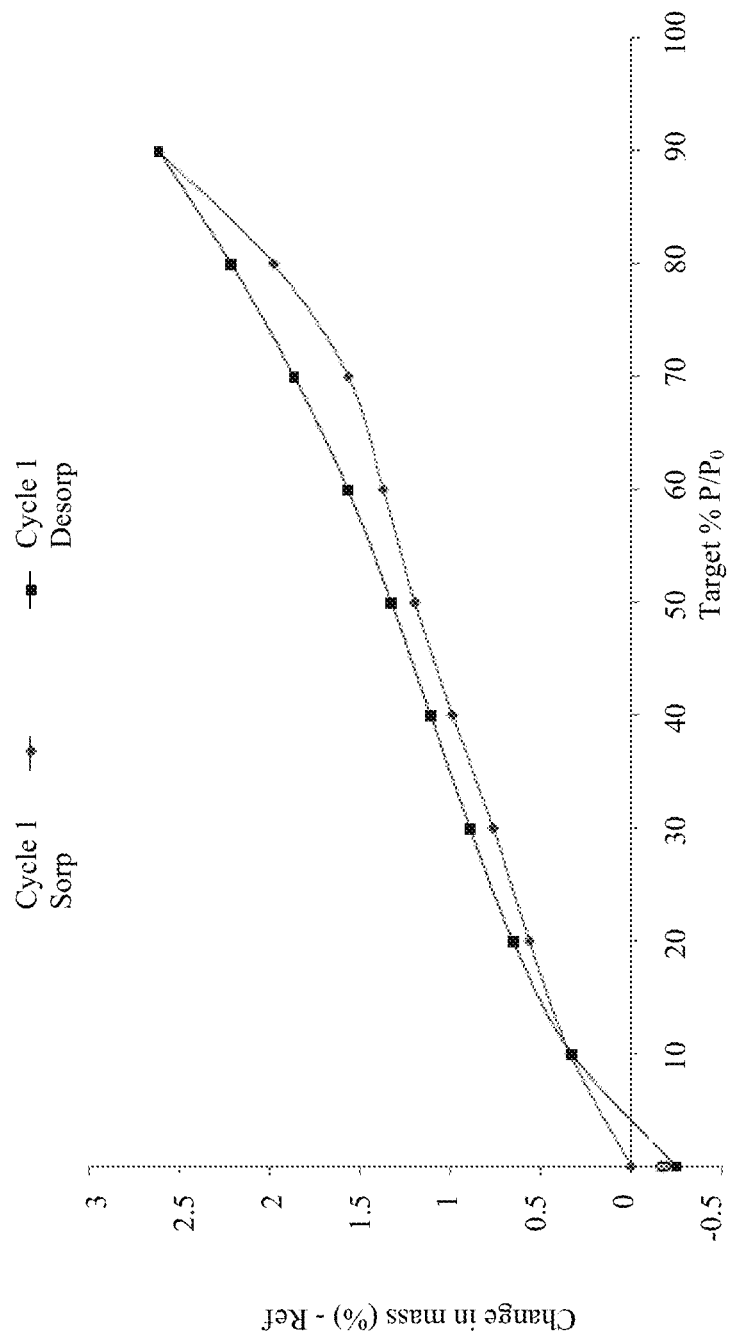
FIG. 17 is a dynamic vapor sorption (DVS) isotherm plot of the amorphous darunavir of the present invention. Sorption is represented by diamonds and desorption is represented by squares.

About 10 mg of amorphous darunavir of the present invention were used to test the hygroscopicity (DVS) from 0% to 90% according to the details on Table 2 hereinabove. The amorphous form of the present invention was found to be hygroscopic (2.617% weight gain from 0% to 90%); FIG. 17).

The amorphous darunavir form of the present invention was further evaluated for its chemical stability. The results are summarized in Table 10. Specifically, about 3 mg of the compound was accurately weighed into a 20 ml clear glass vial and stored under the following conditions: 40° C., 60° C., 40° C./RH 75%, 60° C./RH 75%, and light (25° C.), for 2 weeks. A sample stored at −20° C. was used as control. A slight increase in TRS was found at 40° C., 40° C./75% RH, 60° C. and 60° C./75% RH, while no increase was observed for the amorphous form that was stored under exposure to light at 25° C., both at the end of 1$^{st}$ and 2$^{nd}$ weeks. Additionally, no change was observed in the physical appearance at the end of the 1$^{st}$ and 2$^{nd}$ week for samples stored at 40° C., 40° C./RH 75% and 25° C. under light.

TABLE 10

Solid stability of amorphous darunavir at 40° C., 60° C., 40° C./75% RH, 60° C./75% RH and under light exposure for 7 days and 14 days

| Condition | Time | Sample number | Weight (mg) | Appearance | TRS % | Remaining % |
|---|---|---|---|---|---|---|
| −20° C. | 7 d | 1 | 2.496 | No change | 2.05 | — |
|  |  | 2 | 2.210 | No change | 2.05 |  |
|  | 14 d | 1 | 2.812 | No change | 2.07 | — |
|  |  | 2 | 3.434 | No change | 2.08 |  |
| 40° C. | 7 d | 1 | 3.025 | No change | 3.03 | 97.22 |
|  |  | 2 | 2.861 | No change | 3.07 |  |
|  | 14 d | 1 | 2.780 | No change | 3.35 | 97.40 |
|  |  | 2 | 2.991 | No change | 3.36 |  |
| 60° C. | 7 d | 1 | 2.775 | Stuck | 3.97 | 96.60 |
|  |  | 2 | 2.780 | Stuck | 3.95 |  |
|  | 14 d | 1 | 2.884 | Stuck | 4.04 | 96.08 |
|  |  | 2 | 2.575 | Stuck | 4.00 |  |
| 40° C./75% RH | 7 d | 1 | 2.726 | No change | 3.12 | 96.36 |
|  |  | 2 | 2.681 | No change | 3.29 |  |
|  | 14 d | 1 | 2.385 | No change | 3.64 | 97.10 |
|  |  | 2 | 2.887 | No change | 3.78 |  |
| 60° C./75% RH | 7 d | 1 | 2.644 | Stuck | 4.17 | 94.64 |
|  |  | 2 | 2.660 | Stuck | 4.62 |  |
|  | 14 d | 1 | 3.272 | Stuck | 3.97 | 96.62 |
|  |  | 2 | 2.765 | Stuck | 4.01 |  |
| light | 7 d | 1 | 2.575 | No change | 2.04 | 99.11 |
|  |  | 2 | 2.797 | No change | 2.07 |  |
|  | 14 d | 1 | 2.924 | No change | 2.06 | 100.88 |
|  |  | 2 | 2.580 | No change | 2.06 |  |

The aqueous solubility of amorphous darunavir of the present invention was measured. Specifically, about 10 mg of the compound was accurately weighed into a 4 ml clear glass vial followed by the addition of 2.5 ml buffer (at different pH) to the vial. The vial was then mounted on a Thermomixer and kept shaking for 24 hours at 25° C. The solution was filtered through 0.45 μm PTFE filter. The pH value and concentration of the filtrate were checked by pH meter and HPLC, respectively. The results are summarized in Table 11 and in FIG. 8 panel C.

TABLE 11

Solubility results of amorphous darunavir in aqueous buffers

| Testing media | Solubility (mg/ml) | Appearance | Final pH |
|---|---|---|---|
| water | 0.27 | Many particles | 5.765 |
| pH 1.2 | 1.73* | Many particles | 1.226 |
| pH 4.5 | 0.27 | Many particles | 4.534 |
| pH 6.8 | 0.24 | Many particles | 6.790 |
| pH 7.4 | 0.23 | Many particles | 7.428 |

*degraded

Example 8

Hygroscopicity of Darunavir Ethanolate API

Figure 18:
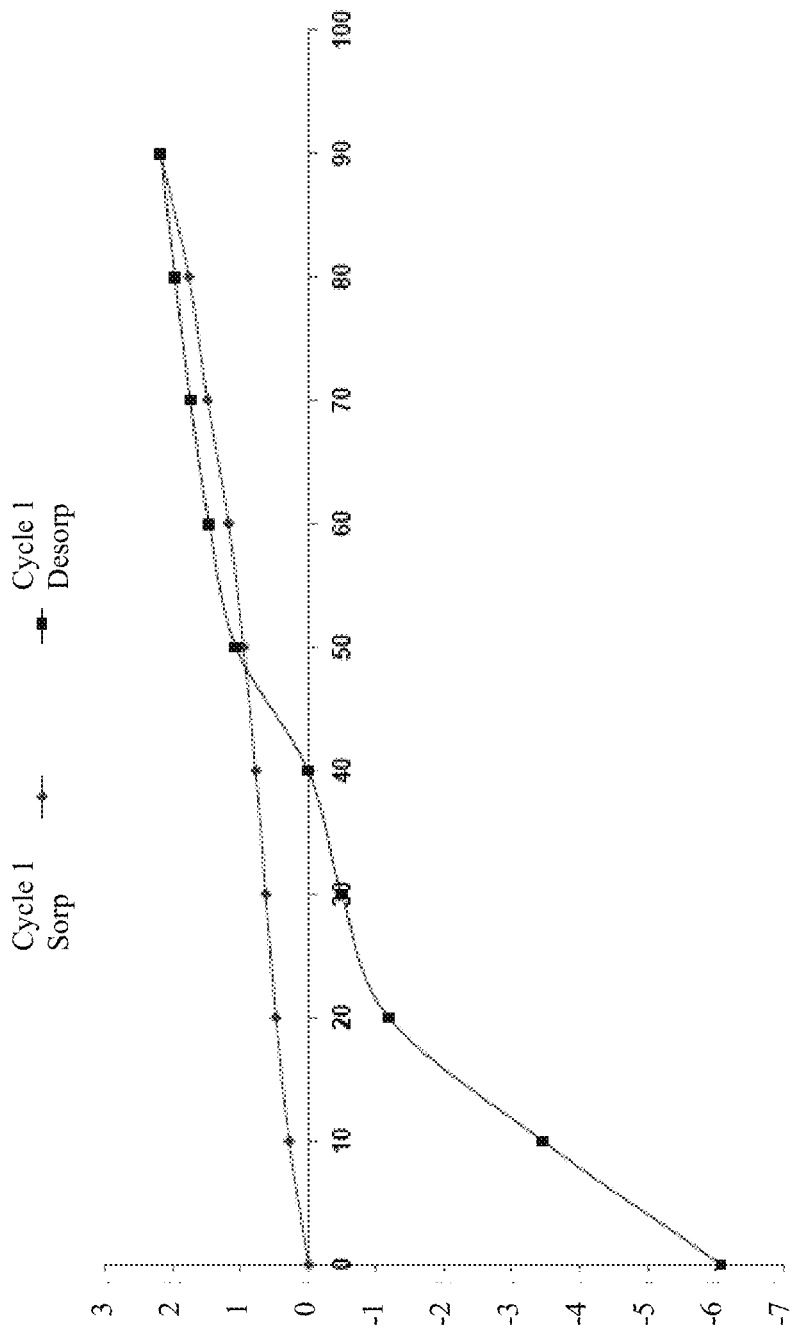
FIG. 18 is a dynamic vapor sorption (DVS) isotherm plot of darunavir ethanolate API. Sorption is represented by diamonds and desorption is represented by squares.

The hygroscopicities of the Darunavir forms of the present invention were compared to the hygroscopicity of Darunavir ethanolate API. Whereas the tetrahydrofuran and dimethylsulfoxide solvates of the present invention were only slightly hygroscopic (1.366% and 0.9431% weight gain from 0% to 90%, respectively), darunavir ethanolate (API) was hygroscopic with 2.180% weight gain from 0% to 90% (FIG. 18). Additionally, darunavir ethanolate lost the solvate ethanol molecules during the desorption measurement.

Thus, the tetrahydrofuran and dimethylsulfoxide solvates of the present invention may possess longer term stability in humid environments and are thus more advantageous for use in the pharmaceutical industry in comparison to darunavir ethanolate.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. An amorphous form of darunavir having an IR spectrum with characteristic peaks at about 1454 and 1369 $cm^{-1}$.

2. The amorphous form according to claim 1, characterized by an IR spectrum with characteristic peaks at about 1454, 1369, 771 and 553 $cm^{-1}$.

3. A solid pharmaceutical composition comprising as an active ingredient the amorphous form of darunavir according to claim 1, and a pharmaceutically acceptable carrier.

4. The pharmaceutical composition according to claim 3, in the form of a tablet.

5. A method of treating retroviral infections or inhibiting retrovirus protease activity comprising administering to a subject in need thereof an effective amount of a composition comprising the amorphous form of darunavir according to claim 1.

6. The method according to claim 5, wherein the retrovirus is HIV and wherein the subject is a human.

7. The method according to claim 5, comprising co-administering the amorphous form of darunavir in combination with at least one other antiretroviral drug, wherein the at least one other antiretroviral drug is ritonavir.

8. A process for preparing the amorphous form of darunavir according to claim 1, the process comprising the steps of:

(a) preparing a saturated solution of darunavir in a solvent or solvent mixture selected from the group consisting of: methyl isobutyl ketone (MIBK), isopropyl acetate (iPrOAc), acetonitrile (ACN), dichloromethane (DCM), ethyl acetate (EtOAc), ACN:Acetone (1:1), Toluene (1:6), DCM:MeOH (1:6), Acetone:MeOH (1:6), ACN: methyl t-butyl ether (MTBE) (1:9), Acetone:MTBE (1:9), 2-MeTHF:MeOH (1:8), and THF:MeOH (1:9); and (b) precipitating the amorphous form of darunavir from said saturated solution.

9. A process for preparing the amorphous form of darunavir according to claim 1, the process comprising the step of precipitating said amorphous darunavir from a solvent/antisolvent system selected from the group consisting of: methyl ethyl ketone (MEK)/Methyl tert-butyl ether (MTBE), $CH_2Cl_2$/Toluene, acetonitrile (ACN)/H2O, 2-MeTHF/IPA and MIBK/Toluene.

* * * * *